United States Patent
Phattaranawik et al.

(10) Patent No.: US 8,135,547 B2
(45) Date of Patent: Mar. 13, 2012

(54) DETECTION APPARATUS AND METHOD UTILIZING MEMBRANES AND RATIO OF TRANSMEMBRANE PRESSURES

(75) Inventors: Jirachote Phattaranawik, Trondheim (NO); Anthony G. Fane, Grays Point (AU); Fook-Sin Wong, Singapore (SG)

(73) Assignee: Nanyang Technological University, Singapore (SG)

( * ) Notice: Subject to any disclaimer, the term of this patent is extended or adjusted under 35 U.S.C. 154(b) by 460 days.

(21) Appl. No.: 12/300,195

(22) PCT Filed: May 10, 2007

(86) PCT No.: PCT/SG2007/000130
§ 371 (c)(1),
(2), (4) Date: Nov. 10, 2008

(87) PCT Pub. No.: WO2007/129994
PCT Pub. Date: Nov. 15, 2007

(65) Prior Publication Data
US 2009/0177412 A1    Jul. 9, 2009

Related U.S. Application Data

(60) Provisional application No. 60/799,011, filed on May 10, 2006.

(51) Int. Cl.
G01N 15/08    (2006.01)
G06F 17/00    (2006.01)
(52) U.S. Cl. .............. 702/35; 702/34; 702/140; 73/38
(58) Field of Classification Search .............. 702/35, 702/34, 50, 140, 185
See application file for complete search history.

(56) References Cited

U.S. PATENT DOCUMENTS

| 4,689,152 | A | 8/1987 | Liang |
| 5,064,515 | A | 11/1991 | Harapanahalli |
| 5,888,401 | A | 3/1999 | Nguyen |
| 6,017,459 | A | 1/2000 | Zeiher et al. |
| 6,066,261 | A | 5/2000 | Spickermann |
| 6,223,130 | B1 * | 4/2001 | Gray et al. ............... 702/51 |
| 6,463,790 | B1 | 10/2002 | Chun et al. |
| 6,986,802 | B2 * | 1/2006 | Colling et al. ............ 95/46 |
| 2007/0089489 | A1 * | 4/2007 | Lewnard et al. ........... 73/38 |

FOREIGN PATENT DOCUMENTS
NL    1021197 C    10/2003

OTHER PUBLICATIONS

Chen et al., "In Situ Monitoring Techniques for concentration polarization and fouling phenomena in membrane filtration", Advances in Colloid and Interface Science, 2004, pp. 83-108, vol. 107, Elsevier B.V. Australian Patent Office, International Search Report mailed Jul. 4, 2007.
Australian Patent Office, Written Opinion of the International Searching Authority mailed Jul. 4, 2007.
Mulhausen, Dorothee, International Preliminary Report on Patentability, issued Nov. 11, 2008.

* cited by examiner

Primary Examiner — Hal Wachsman
(74) Attorney, Agent, or Firm — Dinsmore & Shohl LLP

(57) ABSTRACT

The failure of an upstream filtration membrane, or the presence of a foulant in a fluid is detected using a membrane-based detector. The fluid or an effluent from the filtration membrane is directed to permeate through a first permeable membrane, and from the first membrane to permeate through a second permeable membrane. A ratio between $(P_1-P_2)$ and $(P_2-P_3)$ is determined, where $P_1$ is a first pressure at a feed side of the first membrane, $P_2$ is a second pressure between the first and second membranes, and $P_3$ is a third pressure at a permeate side of the second membrane. The ratio is correlated with the failure of the filtration membrane, or with the presence of the foulant.

33 Claims, 16 Drawing Sheets

DETECTION APPARATUS AND METHOD UTILIZING MEMBRANES AND RATIO OF TRANSMEMBRANE PRESSURES

CROSS REFERENCE TO RELATED APPLICATIONS

This applications claims the benefit of U.S. Provisional Application Ser. No. 60/799,011, filed May 10, 2006, the contents of which are incorporated herein by reference.

FIELD OF THE INVENTION

The present invention relates generally to detection methods and apparatus, and more particularly to apparatus and methods for detecting the integrity of a filtration membrane, or a foulant in a fluid.

BACKGROUND OF THE INVENTION

Membranes used in membrane filtration processes can fail for various reasons. Conventionally, such failures have been detected using techniques such as particle counting or flow content monitoring. A conventional particle counting technique detects laser light scattering caused by particles in the effluent from the filtration membrane. Other techniques for flow content monitoring include particle sensing, turbidity monitoring, and microbial monitoring. These conventional techniques each have drawbacks such as high cost, low sensitivity, or long response time. There are also so called off-line techniques which can only detect failure when the filtration process is suspended or when the filtration membrane is taken off of the production line.

Accordingly, it is desirable to provide an alternative detection technique.

SUMMARY OF THE INVENTION

Thus, in accordance with a first aspect of the present invention, there is provided a method for detecting failure of a filtration membrane. The method comprises directing an effluent from the filtration membrane to permeate through a first permeable membrane, and from the first membrane to permeate through a second permeable membrane; determining a ratio between $(P_1-P_2)$ and $(P_2-P_3)$, $P_1$ being a first pressure at a feed side of the first membrane, $P_2$ being a second pressure between the first and second membranes, and $P_3$ being a third pressure at a permeate side of the second membrane; and correlating the ratio with a failure of the filtration membrane.

The correlating may comprise determining that the filtration membrane is in a failed state when at least one of the ratio and a time derivative of the ratio is higher than a respective threshold. The respective threshold for the ratio may be 3, and the respective threshold for the derivative of the ratio may be 0.01. The ratio may also be correlated with the presence of a foulant in the effluent, such as by determining that the foulant is present in the effluent when the ratio is within a range. The range may be from 0.1 to 50, such as from 1.5 to 3. The ratio may be determined by sensing the first, second, and third pressures, and calculating the ratio at time t, $\pi(t)$, as $\pi(t)=[P_1(t)-P_2(t)]/[P_2(t)-P_3(t)]$. The method may also comprise presenting a correlation result to a user. The flow rate through the first and second membranes may be from 1 to 500 ml/min, such as from 20 to 60 ml/min. The gauge pressure in the feed to the first membrane may be from 1 to 95 kPa, and the gauge pressure in the permeate side of the second membrane may be from −100 to 100 kPa, such as from −100 to 0 kPa. A pressure difference between 0 and 1,000 kPa may be established across the first and second membranes.

In accordance with a further aspect of the present invention, there is provided an apparatus for detecting failure of a filtration membrane. The apparatus comprises a first permeable membrane and a second permeable membrane, each having a feed side and a permeate side; a conduit for directing an effluent from the filtration membrane to the first membrane and from the first membrane to the second membrane; a first pressure sensor for producing a pressure signal indicative of a first pressure, $P_1$, at the feed side of the first membrane; a second pressure sensor for producing a pressure signal indicative of a second pressure, $P_2$, between the first and second membranes; a third pressure sensor for producing a pressure signal indicative of a third pressure, $P_3$, at the permeate side of the second membrane; and a data processing unit in communication with each one of the plurality of pressure sensors. The data processing unit is used for receiving pressure signals from the pressure sensors, calculating a ratio between $(P_1-P_2)$ and $(P_2-P_3)$ based on the pressure signals; and correlating the ratio with a failure of the filtration membrane.

The ratio at time t, $\pi(t)$, may be calculated as $\pi(t)=[P_1(t)-P_2(t)]/[P_2(t)-P_3(t)]$. The correlating may comprise determining that the filtration membrane is in a failed state when at least one of the ratio and a time derivative of the ratio is higher than a respective threshold. The respective threshold for the ratio may be 3, and the respective threshold for the derivative of the ratio may be 0.01. The data processing unit may be adapted to correlate the ratio with the presence of a foulant in the effluent. The data processing unit may be adapted to determine that the foulant is present in the effluent when the ratio is within a range. The range may be from 0.1 to 50, such as from 1.5 to 3. The apparatus may further comprise a fluid pump for establishing a pressure difference across the first and second membranes to drive fluid flow through the first and second membranes. The pressure difference may be between 0 and 1,000 kPa. At least the first membrane may have an average pore size from 0.05 to 5 microns. At least the first membrane may comprise a plurality of membrane layers.

In accordance with another aspect of the present invention, there is also provided a fluid treatment system comprising the apparatus described above and a filtration membrane. The apparatus is in fluid communication with the filtration membrane for receiving an effluent therefrom. The fluid treatment system may further comprise a control unit for controlling operation of the system, the control unit in communication with the data processing unit for controlling the operation in response to the correlating.

In accordance with a further aspect of the present invention, there is provided a method of detecting a foulant in a fluid. The method comprises directing the fluid to permeate through a first permeable membrane and from the first membrane to permeate through a second permeable membrane; determining a ratio between $(P_1-P_2)$ and $(P_2-P_3)$, $P_1$ being a first pressure at a feed side of the first membrane, $P_2$ being a second pressure between the first and second membranes, $P_3$ being a third pressure at a permeate side of the second membrane; and correlating the ratio with the presence of the foulant in the fluid. The correlating may comprise determining that the foulant is present in the fluid when the ratio is higher than a threshold. The threshold may be from 0.1 to 50, such as 1.5. The ratio may be determined by sensing the first, second, and third pressures, and calculating the ratio at time t, $\pi(t)$, as $\pi(t)=[P_1(t)-P_2(t)]/[P_2(t)-P_3(t)]$.

In accordance with another aspect of the present invention, there is provided an apparatus for detecting a foulant in a fluid. The apparatus comprises a first permeable membrane and a second permeable membrane, each having a feed side and a permeate side; a conduit for directing the fluid to the first membrane and from the first membrane to the second membrane; a first pressure sensor for generating a first pressure signal indicative of a first pressure, $P_1$, at the feed side of the first membrane; a second pressure sensor for generating a second pressure signal indicative of a second pressure, $P_2$, between the first and second membranes; a third pressure sensor for generating a third pressure signal indicative of a third pressure, $P_3$, at the permeate side of the second sensor; and a data processing unit in communication with each one of the pressure sensors. The data processing unit is used for receiving the pressure signals from the pressure sensors, calculating a ratio between $(P_1-P_2)$ and $(P_2-P_3)$ based on the pressure signals; and correlating the ratio with the presence of the foulant in the fluid. The ratio at time t, $\pi$ (t), may be calculated as $\pi(t)=[P_1(t)-P_2(t)]/[P_2(t)-P_3(t)]$. The correlating may comprise determining that the foulant is present in the fluid when the ratio is higher than a threshold. The threshold may be 0.1 to 50, such as 1.5. At least the first membrane may have an average pore size from 0.05 to 5 microns.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1A:
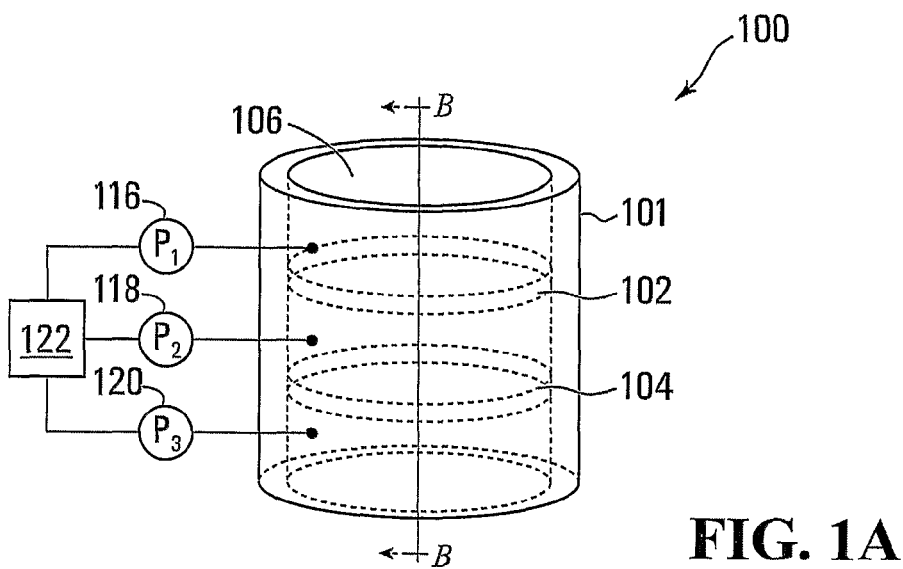
FIG. 1A is a schematic perspective view of a detection apparatus having a membrane module, exemplary of an embodiment of the present invention.
Figure 1B:
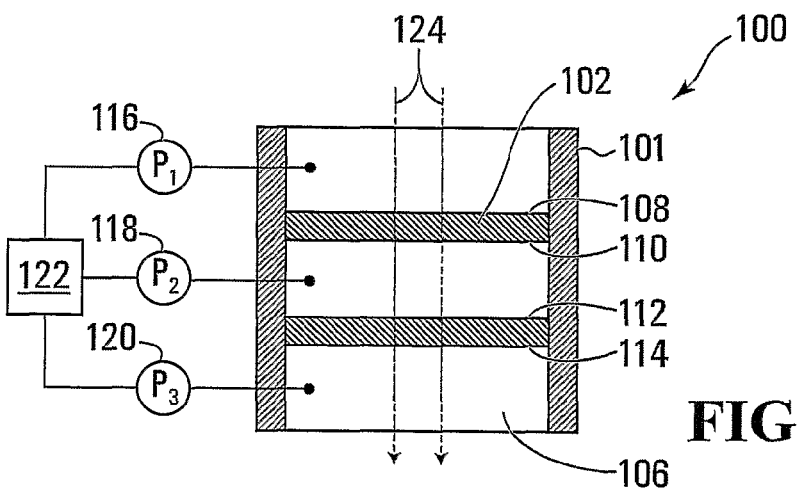
FIG. 1B is a schematic cross-sectional view of the apparatus of FIG. 1A, taken through the central axis B-B.

FIGS. 1A and 1B schematically illustrate a membrane-based detection apparatus 100, exemplary of an embodiment of the present invention. Apparatus 100 includes a membrane module 101, which includes a first membrane 102 and a second membrane 104, which are disposed in a fluid conduit 106 and spaced apart. Membrane 102 has a feed side 108 and a permeate side 110, and membrane 104 has a feed side 112 and a permeate side 114. Pressure sensors 116, 118, 120 are disposed in conduit 106 for sensing a pressure ($P_1$) at feed side 108 of membrane 102, a pressure ($P_2$) between membranes 102 and 104, and a pressure ($P_3$) at permeate side of membrane 104, respectively. Pressure sensors 116, 118, 120 are in communication with a data processing unit 122, which is adapted to process the pressure signals received from pressure sensors 116, 118, 120 and correlate a result of such processing with a state to be detected, as will be detailed below.

As depicted, membranes 102, 104 may have a generally disk shape. In one embodiment, each membrane 102, 104 may have a cross-sectional area of about 0.6 cm$^2$ and a thickness of about 125 microns. In a different embodiment, the thickness may be from 20 to 500 microns. The shape or the size of each membrane 102, 104 may vary in different embodiments. For example, the cross-sectional area of each membrane 102, 104 may be from 0.1 cm$^2$ to 100 cm$^2$.

Each membrane 102, 104 is a permeable membrane. A permeable membrane selectively allows some substances to permeate therethrough but do not allow others to pass through. Thus, each membrane 102, 104 is porous and allows a permeate to pass through from its feed side to its permeate side. For example, membrane 102 may be micro-porous and may have an average pore size of 0.05 to 5 microns. Membrane 104 may have a similar or different structure. Membrane 104 may have a smaller average pore size than that of membrane 102. The average pore size of a membrane may be determined using any suitable technique known in the art. For example, the pore size may be determined in terms of the sizes or diameters of particles a membrane is likely to retain to a selected degree of efficiency.

Membrane 102 is selected so that a given foulant when fed to membrane 102 can cause fouling of membrane 102. Fouling is a process that results in a decrease in performance of a membrane, caused by the deposition of suspended or dissolved solids on the external membrane surface, on the membrane pores, or within the membrane pores. A typical foulant is particles that have sizes larger than the pore sizes of membrane 102. Other types of potential foulant are known to those skilled in the art, and may include other materials that are highly adsorptive on the membrane surface due to their chemical or physical properties. Thus, the material and structure of membrane 102 (and membrane 104) may vary and be selected depending on the intended application.

Various suitable membrane materials are commercially available. Exemplary membrane materials that may be used in membrane 102 or 104 include cellulose acetate (CA), hydrophilic polyvinylidenefluoride (PVDF), hydrophobic PVDF, hydrophobic polytetrafluoroethylene (PTFE), or the like. The pore sizes in these membrane materials may vary such as from 0.2 to 0.8 microns. The pore size may be selected so that the selected foulant, such as large particles, will foul at least the first membrane 102. For example, a CA membrane may have an average pore size of 0.2, 0.4, or 0.8 microns; a PVDF membrane may have an average pore size of 0.22 or 0.45 microns; and a hydrophobic PTFE membrane may have an average size of 0.45 or 1.0 microns.

As alluded to earlier, the membranes in the membrane module may have the same or different characteristics, properties and structures. Each membrane 102, 104 may be formed of a single membrane material or a combination of different materials. For example, each membrane 102, 104 may be formed of a single membrane layer or multiple membrane layers, where each membrane layer may be formed of a different membrane material or may have different pore characteristics, such as different pore sizes or porosity. Different membranes or membrane layers may also have different thickness.

Figure 1C:
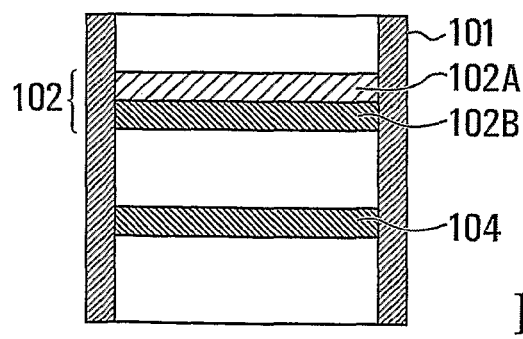
FIGS. 1C, 1D, and 1E are partial sectional views of alternative embodiments of the membrane module of FIGS. 1A and 1B.
Figure 1D:
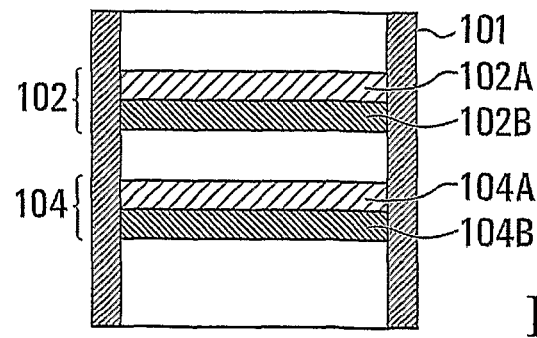

To illustrate, some alternative embodiments of membrane module 101 are shown in FIGS. 1C to 1D. As shown in FIG. 1C, in one embodiment membrane 102 may have two membrane layers 102A and 102B, and membrane 104 may have a single layer. As shown in FIG. 1D, in another embodiment both membranes 102 and 104 may be double-layered. Membrane layers 102A, 102B, 104A, 104B may differ in their chemical or physical properties, such as pore sizes, constituent materials, thicknesses, or the like.

Figure 1E:
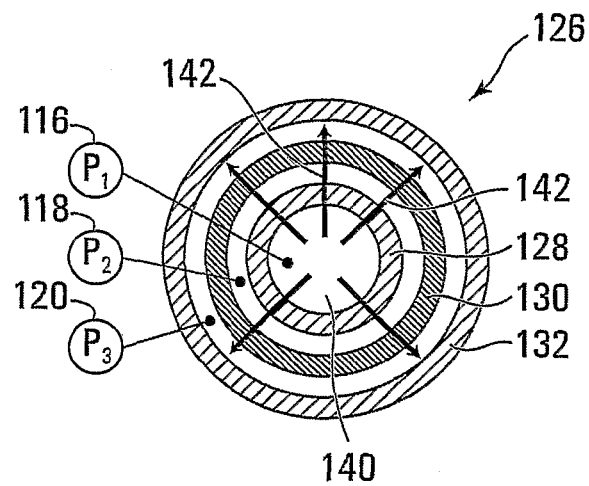

FIG. 1E illustrates a tubular membrane module 126, which may be used in place of membrane module 101. Membrane module 126 includes an inner tubular membrane 128 (corresponds to membrane 102), an outer tubular membrane 130 (corresponds to membrane 104), and tubular housing 132. A fluid 142 may be fed to the inner fluid channel 140, and permeate through membranes 128, 130. The permeate is collected from between membrane 130 and housing 132. Pressure sensors 116, 118, 120 may be disposed in the fluid path as indicated.

Conduit 106 may have a circular cross-section or a different shape such as square, rectangular, oval or the like. The cross-sectional area may also vary. In one embodiment, the cross-sectional area may be about 0.6 cm$^2$. The material, shape and size of conduit 106 may be selected to be compatible with membranes 102 and 104, and to meet the requirements of the intended application. For example, the module body defining conduit 106 may be formed of a material that is resistant to selected chemicals, such as acids, bases, solvents, or the like. The material may be, for example, resistant to NaOCl. The material may also be selected so that it is relatively easy to machine and remains functional in a wide range of temperatures, such as from 0 to 150° C. Suitable materials may include stainless steel 316, chemical-resistant polymeric plastics such as acrylic or poly(methyl methacrylate), solid Teflon, polycarbonate, or the like.

Pressure sensors 116, 118, 120 may include electronic pressure transducers or any other suitable pressure sensors. The output signal from an electronic pressure transducer may be digital, or analog. In case the signal is analog, an analog-to-digital converter (not shown) may be provided to convert the signal to a digital signal. The output signal may include a voltage or a current signal, or both voltage and current signals. The output signals vary depending on the fluid pressures in the respective region of conduit 106. The pressure sensors may be selected so that the output signal is linearly dependent on the pressure in the corresponding region.

Each pressure sensor may be selected so that it is suitable for sensing pressures in a selected pressure range, such as from −100 kPa to 10,000 kPa. The portion of a pressures sensor, and the port (not shown) that connects the pressure sensor to conduit 106, that may be potentially exposed to fluid 124 should be resistant to chemicals present in fluid 124. For example, the connection port may be made of stainless steel 316, or like materials. The pressures sensors may also be selected for operation in a selected range of temperatures, such as from 0 to 150° C.

While not shown, it can be understood that a pressure sensor may have a threaded body portion for engaging a connection port in module 101. For example, the threaded body of the pressure sensor may include a male thread, and the connection port may have a matching female thread. The threaded body may have a diameter of ¼ inch or ⅛ inch.

Data processing unit 122 may include communication components (not shown) for receiving pressure signals from pressure sensors, and a processor (not shown) for calculating the transmembrane pressure (TMP) for each of membrane 102 and 104, based on the pressure signals, and a ratio of the transmembrane pressures. A transmembrane pressure for a membrane is the pressure difference across the membrane, or, the difference between the pressure at the feed side and the pressure at the permeate side. As will be further discussed below, a ratio of the transmembrane pressures is indicative of the performance of membrane 102, and the ratio may be correlated to the presence of any foulant in the feed to membrane 102, or correlated to whether an upstream filtration membrane has failed. Data processing unit 122 may be adapted to perform such correlations and communicate the correlation result to the user. Alternatively, Data processing unit 122 may be adapted to report or communicate the ratio to a user or another computing device to do the correlation.

As will become clear, data processing unit 122 may include any suitable computing or control hardware that are used in computing and control systems, include conventional hardware and standard components. For example, a standard computer processor (not shown) may be used, and a standard proportional-integral-derivative (PID) controller (not shown, but see FIG. 4) may be used in data processing unit 122. Data processing unit 122 may also include a computer such as a portable or personal computer, or the like (not shown, but see FIG. 4). The conventional components or hardware, such as a controller or computer, may be programmed to perform the necessary and optional functions and calculations, described herein. Data processing unit 122 may also include other components and software for various purposes, including memory storage, data communication, input/output, display devices and the like, as can be understood by persons skilled in the art. The memory storage may store both data and computer-executable codes for adapting a processor in communication therewith to perform certain functions and calculations described herein.

Figure 2:
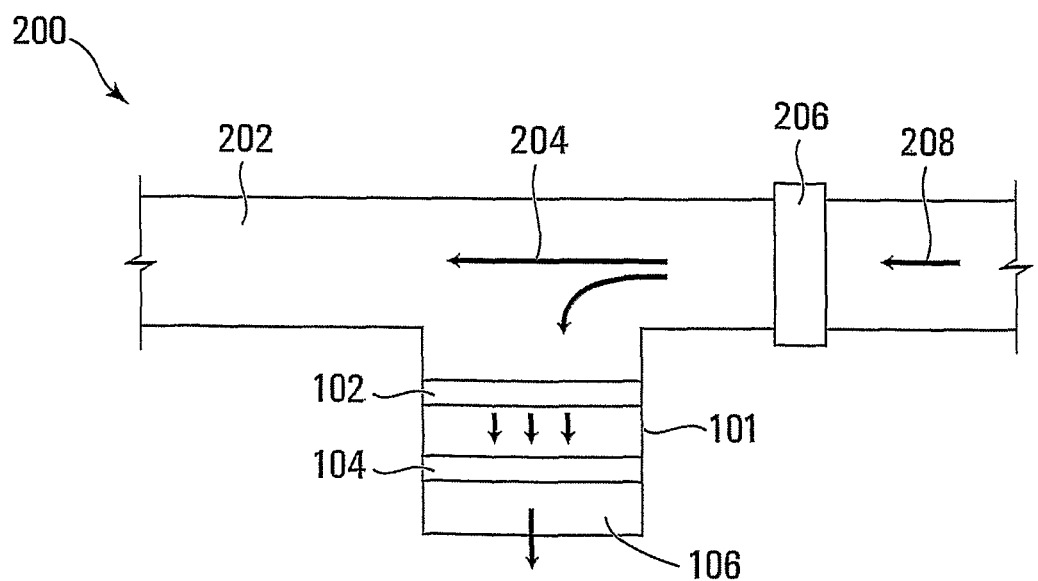
FIG. 2 is a schematic partial cross-sectional view of a water treatment system, incorporating the apparatus of FIG. 1A, exemplary of an embodiment of the present invention.

Apparatus 100 may be used as a membrane integrity detector, as illustrated in FIG. 2. For simplicity, only membrane module 101 of apparatus 100 is shown in FIG. 2 and certain features of apparatus 100 such as the pressure sensors and the data processing unit are omitted. A portion of a membrane-based fluid treatment system 200 is also shown in FIG. 2. As depicted, system 200 includes a pipe 202 for receiving an effluent 204, which is the permeate from an upstream filtration membrane 206. The feed to filtration membrane 206, also referred to as influent 208, may be wastewater or any fluid to be treated or filtered. Apparatus 100 is in communication with pipe 202 for receiving at least a portion of effluent 204 into conduit 106 as the feed to membrane 102. Apparatus 100 can be used to detect the failure of filtration membrane 206, while a continuous flow of influent 208 and effluent 204 is maintained.

A filtration membrane fails when the permeate from the membrane contains a substantial amount of a substance that should not have been present in the permeate had the filtration membrane is in a normal working condition. A filtration membrane can fail for a number of reasons. For example, the fibers in the filtration membrane may break, thus the pore sizes become larger, or a hole or crack may develop through the membrane.

For the purpose of illustration, it is assumed that influent 208 contains a foulant with respect to membrane 102. That is, when the foulant is fed to membrane 102, membrane 102 will start fouling. It is also assumed that, when filtration membrane 206 is in normal operating conditions, filtration membrane 206 will filter out or retain at least most of the foulant, so that effluent 204 is substantially free of such foulant. But when filtration membrane 206 fails, the foulant will be present in effluent 204 and fed to membrane 102.

As shown in FIGS. 1B and 2, in operation, at least a portion of effluent 204 is directed into conduit 106 to flow through membrane 102 and then membrane 104, as indicated by the arrows 124. The flow through membranes 102, 104 may be induced by establishing a pressure difference across membranes 102 and 104, by pressurizing feed side 108 (referred to as pressurization mode), drawing fluid from permeate side 114 (referred to as vacuum or suction mode), or both (pressurization-suction mode). One or more fluid pump (not shown, but see FIGS. 4 and 6) may be used to establish the pressure difference across membranes 102, 104. The flow rate through conduit 106 may be relatively low, such as from 20 to 60 ml/min. In a different embodiment, however, the flow rate may be vary from 1 to 500 ml/min. The total pressure difference across membranes 102 and 104 may be between 0 and 1,000 kPa. When operating in the pressurization mode, a pressure from 1 kPa to 95 kPa (gauge pressure) may be applied at feed side 108 of membrane 102, and the pressure at permeate side 114 of membrane 104 may be lower, such as at the environmental or atmospheric pressure. In a suction mode, the pressure at permeate side 114 of membrane 104 may be from −100 kPa to 100 kPa, such as from −100 kPa to 0 kPa (gauge pressure), and the pressure at feed side 108 of membrane 102 may be higher, such as at the environmental or atmospheric pressure.

Pressure $P_1$ in the fluid flow at feed side 108 of membrane 102 is sensed and monitored by pressure sensor 116. Pressure $P_2$ in the fluid flow between membranes 102 and 104 is sensed and monitored by pressure sensor 118. Pressure $P_3$ in the fluid flow at permeate side 114 of membrane 104 is sensed and monitored by pressure sensor 120.

The pressure signals produced by pressure sensors 116, 118, 120 are communicated to and received by data processing unit 122.

In a particular embodiment, data processing unit 122 may calculate a ratio $\pi$ in response to receiving the detected pressure signals at time t as:

$$\pi(t)=[P_1(t)-P_2(t)]/[P_2(t)-P_3(t)]. \quad (1)$$

As can be appreciated, $[P_1(t)-P_2(t)]$ is the transmembrane pressure for membrane 102, $[P_2(t)-P_3(t)]$ is the transmembrane pressure for membrane 104, and $\pi$ is a ratio of the two transmembrane pressures. The ratio $\pi(t)$ may vary over time and may be correlated with the presence of the foulant in effluent 204 and consequently, a failure of upstream filtration membrane 206, as will be explained next. For brevity, $\pi(t)$, $P_1(t)$, $P_2(t)$, and $P_3(t)$ are also denoted as $\pi$, $P_1$, $P_2$, and $P_3$ herein but it should be understood that these parameters may be time dependent. The pressures may be expressed either as absolute or gauge pressures, as long as they are expressed consistently in equation (1).

When effluent 204, and hence flow 124, is substantially free of the foulant, it is expected that the value of $\pi$ will remain relatively constant, and its time derivate $d\pi/dt$ will be zero or close to zero. However, when effluent 204 and flow 124 contains a significant amount of the foulant, membrane 102 will start fouling. As a result, the membrane performance will deteriorate and the value of $\pi$ will increase. The rate of change in $\pi$, i.e. the time derivative $d\pi/dt$, may also increase because slow fouling may exist when filtration membrane 206 has not failed but after failure, the fouling rate may become significantly faster thus giving rise to a higher $d\pi/dt$. Thus, the ratio $\pi$ or its time derivative $d\pi/dt$ can be correlated to failure of the upstream filtration membrane 206. In some cases, $d\pi/dt$ may be more sensitive to the presence of the foulant or failure of the filtration membrane than $\pi$.

Specifically, when filtration membrane 206 fails, the foulant in influent 208 can pass through filtration membrane 206 and will be present in effluent 204 and subsequently fed to membrane 102. The substantial amount of foulant in the feed to membrane 102 will result in fouling of membrane 102, which consequently causes a significant increase in $\pi$ and $d\pi/dt$. Therefore, by monitoring the change in $\pi$, or $d\pi/dt$, the integrity of the upstream filtration membrane 206 can be monitored.

The ratio $\pi$ or $d\pi/dt$ may be correlated to the operational status of filtration membrane 206 as follows.

A normal operational range and a failure range may be pre-selected for each of $\pi$ and $d(\pi)/dt$. For illustration purposes, it is assumed that for $\pi$ the normal range is from a to b, and the failure range is higher than a threshold c, where a, b, and c are constants. The corresponding constants for $d(\pi)/dt$ are respectively denoted with a subscript "d" as $a_d$, $b_d$ and $c_d$. The values of these constants may be pre-selected based on calculations, experience, or test results. Different values may be used depending on the particular application. Many factors such as operating pressures, the nature of the fluids involved, the fluid flow rates through both membrane 102 and 104, and the like, may affect the selection of these valves. In some cases, the values may be determined through test runs. For example, a clean test fluid free of any foulant and test fluids containing known amounts of the foulant may be used in separate test runs to determine the ranges and thresholds. The value of b or $b_d$ may be selected somewhat arbitrarily, as long as it is adequate to set a threshold for indicating significant fouling. The constants may be adjusted during a monitoring period.

In one embodiment, the parameters may be selected as $a=a_d=0$, $b=1.5$, $b_d=0.001$, $c=3$, $c_d=0.01$. In another embodiment, a, b, and c may each have a value selected from the range of 0 to about 100; and $a_d$, $b_d$, and $c_d$ may each have a value selected from the range of 0 to about 10. The parameter b may have a value from 0.1 to 50 in some embodiments. As can be understood, these parameters should satisfy the conditions that $a<b<c$ and $a_d<b_d<c_d$.

When $$a<\pi<b, \text{ or } a_d<d\pi/dt<b_d, \quad (2)$$

it may be determined that upstream filtration membrane 206 is currently in a normal working state.

When $$\pi>c, \text{ or } d\pi/dt>c_d, \quad (3)$$

it may be determined that upstream filtration membrane 206 is in a failed state.

When $$b\leq\pi\leq c, \text{ or } b_d\leq d\pi/dt\leq c_d, \quad (4)$$

it may be determined that effluent 204 contains a certain amount of the foulant, but upstream filtration membrane 206 is still not in a failed state.

While either $\pi$ or $d\pi/dt$ may be used alone, using both criteria may provide better sensitivity, accuracy or reliability in some applications.

Depending on which one of equations (2) to (4) is true, different actions may be taken by the data processing unit, a control unit (not shown) for system 200, or a human operator.

For example, if equation (2) is true, the upstream filtration process may be allowed to continue. Optionally, a signal indicating a normal operating condition, such as "Operation Normal", may be generated, displayed to a user, or transmitted to a remote location. In response to this signal, an ongoing filtering process may be allowed to continue, or a new treatment process may be started, based on the expectation that the upstream treatment system is in good working conditions. One or more triggering conditions may be pre-set, and when such triggering conditions are detected, certain appropriate actions or response can be taken, either automatically by a control unit or by a human operator.

Figure 5:
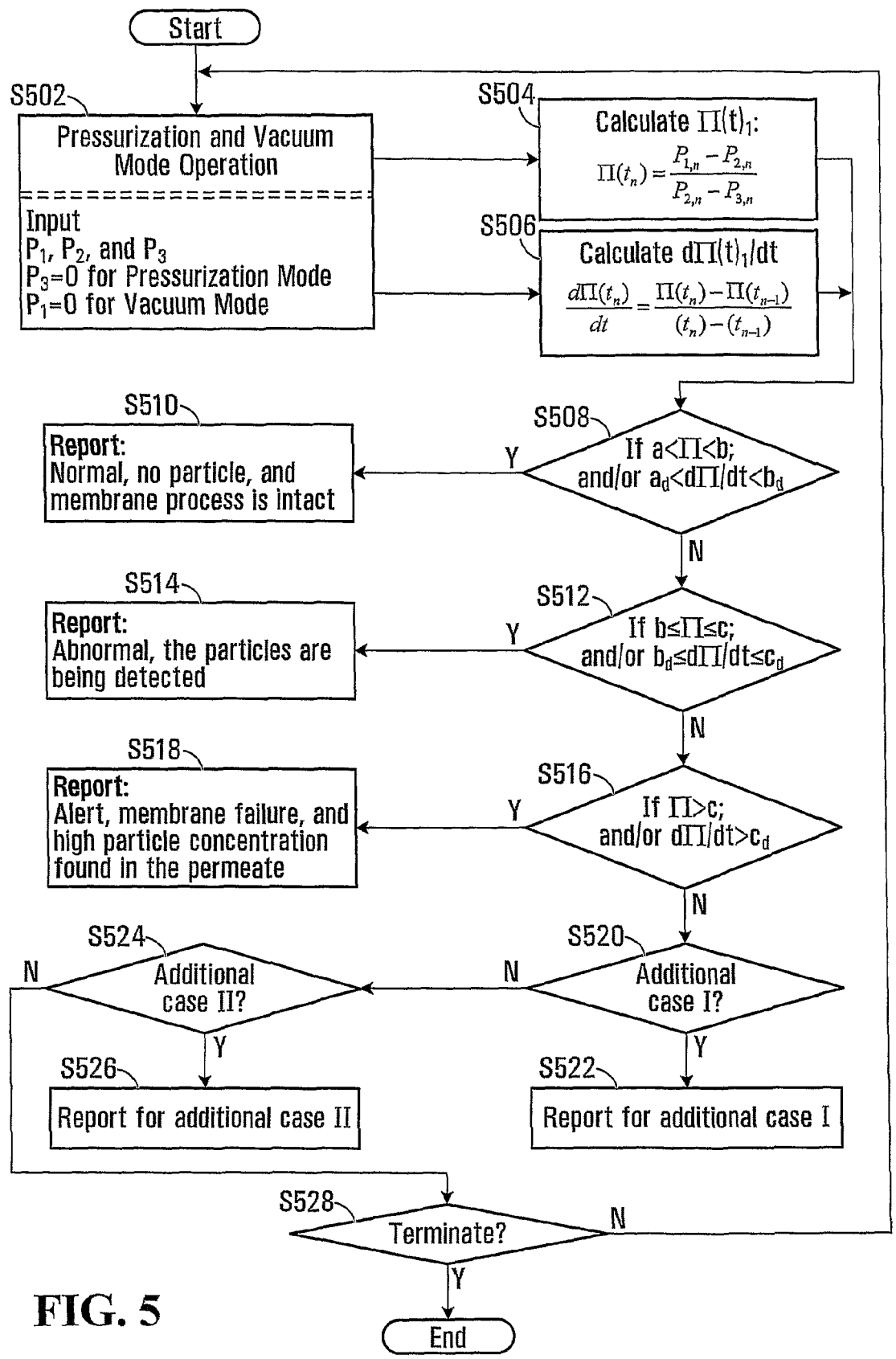
FIG. 5 is a flow chart for an algorithm performed by the control unit of the membrane-based detector of FIG. 3.

If equation (3) is true, a signal such as "Membrane Failure", may be generated and displayed, or otherwise communicated, to a user or a control unit (not shown, but see FIG. 5). The signal may be transmitted to a remote location such as through a network including the Internet. An audio or visual signal may also be generated to alert the operator or another user. In response to receiving the failure signal, the user or a control unit for the system may react by taking appropriate actions, such as suspending the filtration process, replacing or repairing the failed or broken membrane, or like actions. Thus, the system may be monitored and controlled remotely.

If equation (4) is true, it can be expected that some fouling is occurring, indicating that the foulant is present in effluent 204 but not in an amount large enough to indicate failure of filtration membrane 206. Optionally, a signal such as "Operation Abnormal" may be presented to a user for the user to take notice or take appropriate action. For example, it may be that a re-circulated carrying fluid used in the system may need to be replaced, or an upstream fluid container may require cleaning, or the upstream filtration membrane 206 may be near its lifetime and may need to be replaced before it actually fails. Thus, precautionary actions may also be taken.

The embodiments of present invention described above may provide certain benefits. For example, the state or integrity of a filtration membrane may be monitored on-line continuously using detection apparatus 100. The detection apparatus may be relatively simple and inexpensive to construct and operate. For instance, the pressure sensors may be relatively inexpensive and the electronic communication among the pressure sensors, data processing unit, and possible control unit can be implemented using conventional techniques which may also be relatively inexpensive. For instance, a conventional computer may be used as part of the data processing and control unit, which may already be provided in an existing plant. Thus, additional equipment cost may be avoided. The use of an embodiment of the present invention can also reduce maintenance cost. The detection apparatus may be relative compact.

The low cost and simplicity of embodiments of the present invention may make them suitable for de-centralized or small fluid treatment systems or plants. For large treatment plants, implementation of an embodiment of the present invention may also be relatively inexpensive.

The embodiments described above do not require highly skilled operators to operate and maintain. The components of the apparatus may all be of a type commonly used in a typical fluid treatment plant, and no special components are required. Thus, labor costs may also be low because no special skills or training are required.

Apparatus 100 may also be conveniently used to perform other functions instead of monitoring the integrity of an upstream membrane. For example, it may be used in on-line fluid quality test, e.g. water quality test in a Reverse-Osmosis (RO) wastewater treatment plant, in place of a silt density index (SDI) test. It may also be used to detect the presence of a certain foulant, such as particles in a solution.

For example, the relationship between the concentration of a selected foulant and the ratio $\pi$ (or $d\pi/dt$) may be predetermined using fluids containing different known concentrations of the foulant. This relationship may be stored as a database, a table, a chart, an empirical formula or the like. The detected ratio $\pi$ (or $d\pi/dt$) during actual operation may be compared with the stored values, or used as inputs to the empirical formula, to derive the measured concentration of the foulant in a tested fluid.

As the ratio $\pi$ is insensitive to change in flow rate, precise flow rate control may not be required.

The embodiments described above may be modified, for example, as described below.

In some different embodiments, $\pi$ may be calculated in a simplified and approximate manner. For example, when $P_2 \gg P_3$, equation (1) may be simplified as:

$$\pi(t) \approx [P_1(t)-P_2(t)]/P_2(t). \tag{1a}$$

When $P_1 \gg P_2$, and $P_2 \gg P_3$, equation (1) may be simplified as:

$$\pi(t) \approx P_1(t)/P_2(t). \tag{1b}$$

In both of these cases, it is not necessary to monitor the pressure $P_3$. The equation (1A) or (1B) may be used to calculate $\pi$, when $P_1$ is relatively high and $P_3$ remains close to 0 (gauge pressure). This condition may exist, for example, when apparatus 100 is operating in a pressurization mode. While for equation (1) the pressures may be expressed as absolute or gauge pressures, in equations (1a) and (1b), the pressures should be expressed as gauge pressures.

Alternatively, $\pi$ may also be calculated in other suitable manners. For example, the transmembrane pressures in equation (1) may be inversed.

When $\pi$ is calculated using a different form or equation, the range and threshold parameters in equation (2) to (4) may be different, and may need to be adjusted or re-selected.

Different forms of $\pi$ may provide different performance in a given application. Thus, an optimal form of $\pi$ may be selected in a given embodiment. For instance, one form may provide better sensitivity in a given situation than another form. In some applications, it is desirable to keep the monitoring process and apparatus simple, in which case, a simplified form of $\pi$ may be used when the simplified form can provide acceptable result. A suitable form of $\pi$ should be a reliable indicator of the reduction in membrane performance due to fouling, and be insensitive to external factors such as upstream flow rate or pressure changes, downstream pressure changes, or the like.

As between equations (1) and (1b), simulation calculations showed that the form of (1) is more sensitive to fouling than the form of (1b). It has been found that after upstream membrane failure, the normalized $\pi$, $\pi_{normal}=\pi(t=t_{current})/\pi(t=0)$, would increase significantly with time if $\pi$ was calculated using equation (1), but only increase slightly if calculated using equation (1b).

It is also possible that $\pi$ be calculated using an equation different from (1), (1a) and (1b), including a suitable polynomial or exponential function of $P_1$ and $P_2$, and optionally $P_3$ or the respective transmembrane pressures. It is possible in some applications, a more complicated form of $\pi$ may produce better sensitivity. It may also be desirable that the selected form of $\pi$ provides sufficient sensitivity or a relatively short response time. The response time is the time it takes for the membrane detector to indicate failure after actual failure. When the response time is short, the membrane detector is considered to have good sensitivity. For certain applications, such as in a wastewater treatment plant, a response time on the order of 10 to 90 minutes may be adequate.

When selecting a suitable form for $\pi$, one may consider whether the form provides good stability, that is, how much $\pi_{normal}$ varies under normal working conditions. For instance, it may be advantageous if the fluctuation of $\pi_{normal}$ during normal operation is within 5%.

It is noted that when $P_1$ and $P_3$ are maintained at constant levels, a change, such as a sudden decrease, in the pressure $P_2$ by itself or the permeate flux through membrane 102, may indicate a change in the fluid content, such as due to a failure of the upstream filtration membrane. However, such an indication is not always reliable. This is because $P_2$ and the permeate flux are dependent on $P_1$ and $P_3$, and a change in $P_2$ can be the result of a change in $P_1$ or $P_3$, or both $P_1$ and $P_3$. $P_1$ or $P_3$ may change due to various reasons including system fluctuation, temperature changes, upstream fluid pressure changes, upstream effluent flow rate changes, or the like. In the suction mode, $P_3$ may also change if the applied suction pressure changes. In contrast, a ratio of the transmembrane pressures can provide a more reliable indication of the state of the upstream membrane. Generally, a ratio of the transmembrane pressures is less sensitive to system fluctuation and other external factors than the individual pressures or individual transmembrane pressures are. A function of the ratio is also relatively insensitive to the external factors. Thus, the ratio or a function of the ratio may be advantageously used for calculating $\pi$. In this regard, and for clarification, correlating a ratio to a particular state includes correlating a function of the ratio to the state.

The correlation between ratio $\pi$ and the state or event to be determined, such as the failure of an upstream filtration membrane, may be by way of correlating a selected function of $\pi$ to the respective state or event. For instance, the function of $\pi$ may be its derivative, a polynomial function of $\pi$ (such as $\pi^2$ or the like), a trigonometric function of $\pi$ (such as $\sin(\pi)$ or the like), or an exponential function (such as $\exp(\pi)$ or the like). Other more complicated functions of $\pi$ may also be used.

It has also been found that operating the detection apparatus under relatively low pressures can improve stability. In this regard, it may be advantageous to keep the gauge pressure at the feed side of the first membrane below 95 kPa.

While the conduit 106 depicted in FIGS. 1A and 1B has a cylindrical shape, it should be understood that in different embodiments the conduit may have other shapes and sizes. Accordingly, membranes 102 and 104 may also have different shapes and sizes. The shapes and sizes of the conduit and the membranes may be dictated by the particular applications in which the apparatus is used, or may be selected based on other factors such as availability, functionality, cost, compatibility, and the like.

While flat-sheet membranes are depicted in FIGS. 1A, 1B and 2, other types of membrane modules may be used. For instance, hollow fibers, tubular, or spiral-wound membranes may be used. Instead of cross-flow arrangement, a dead-end flow or co-current flow arrangement may be used.

In stead of directly connected to the existing downstream fluid path of the filtration membrane, the membrane-based detector may be connected indirectly to the upstream membrane. For instance, an effluent reservoir may be provided between the sensor apparatus and the system fluid path, which may include a fluid tank. The tank may be pressurized to provide the pressurization needed to drive fluid through the sensor membranes.

Optionally, a disinfectant, such as NaOCl, may be injected into the feed stream to the membrane-based detector to improve performance. NaOCl can reduce biofouling on the membrane 102 and 104. Biofouling may cause increase of $\pi$, but may not be indicative of failure of the upstream membrane. The concentration of NaOCl in the feed to membrane 102 should be limited to a suitable level, as high concentration NaOCl may also inhibit other types of fouling including physical fouling, such as due to deposition of large particles that are present due to failure of the upstream membrane. When NaOCl is to be added, membranes 102, 104 should be made of materials that are compatible with NaOCl.

Figure 3:
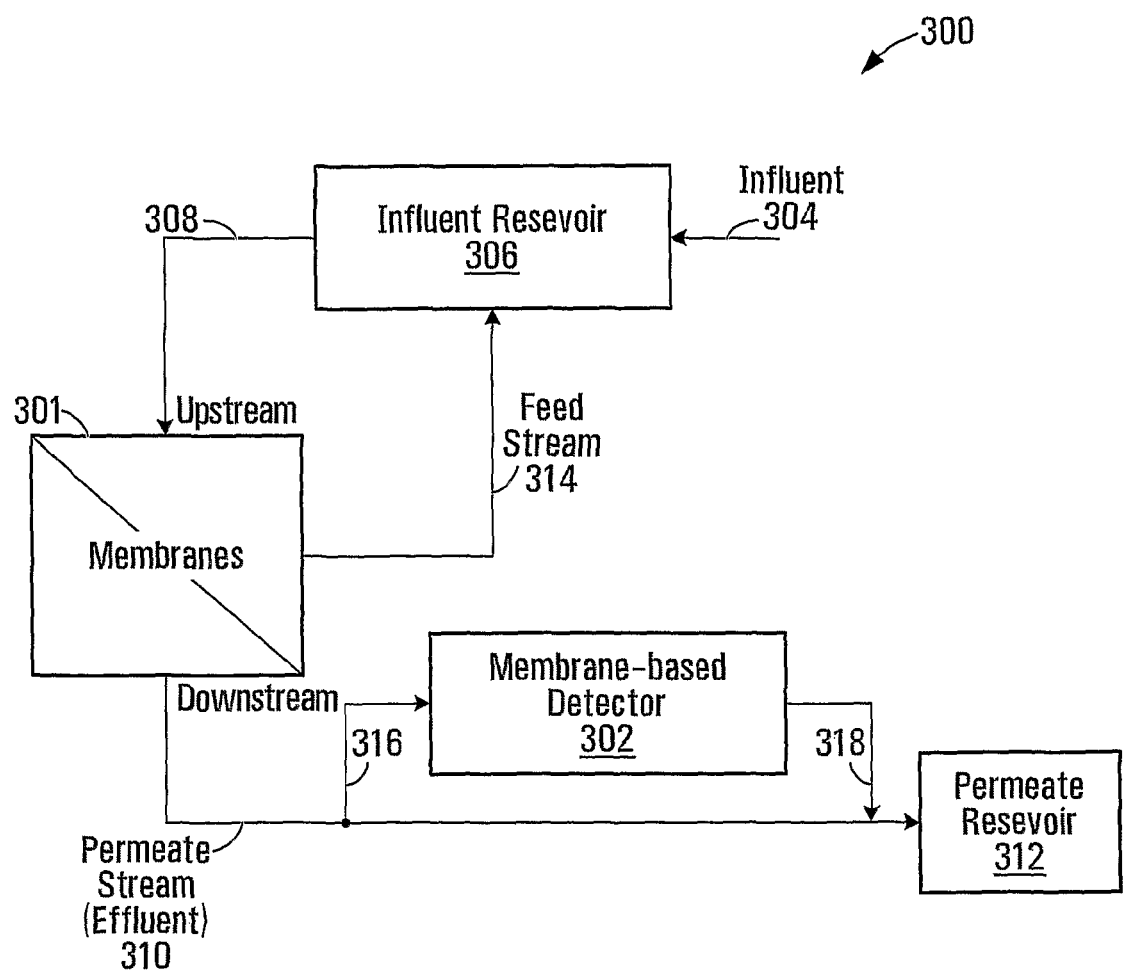
FIG. 3 is a schematic diagram of a fluid treatment plant including a membrane-based detector, exemplary of an embodiment of the present invention.

FIG. 3 schematically illustrates a possible arrangement of a filtration membrane plant 300 incorporating a membrane-based detector 302, exemplary of an embodiment of the present invention.

Plant 300 receives an influent 304, which is initially stored in an upstream influent reservoir 306. Plant 300 may include one or more filtration (including any separation) membranes 301. Influent 304 is fed to membrane(s) 301 through input pipeline 308. The downstream permeate stream is transported through pipeline 310 to a permeate reservoir 312. A return pipeline 314 transports the feed fluid remaining on the upstream side back to influent reservoir 306 for re-circulation. Detector 302 is connected in parallel to a portion of pipeline 310 by feed line 316 and permeate line 318. Fluid control components, such as valves, gauges, pumps and the like (not shown, but see FIG. 4) may be provided, as will be understood by those skilled in the art.

Figure 4:
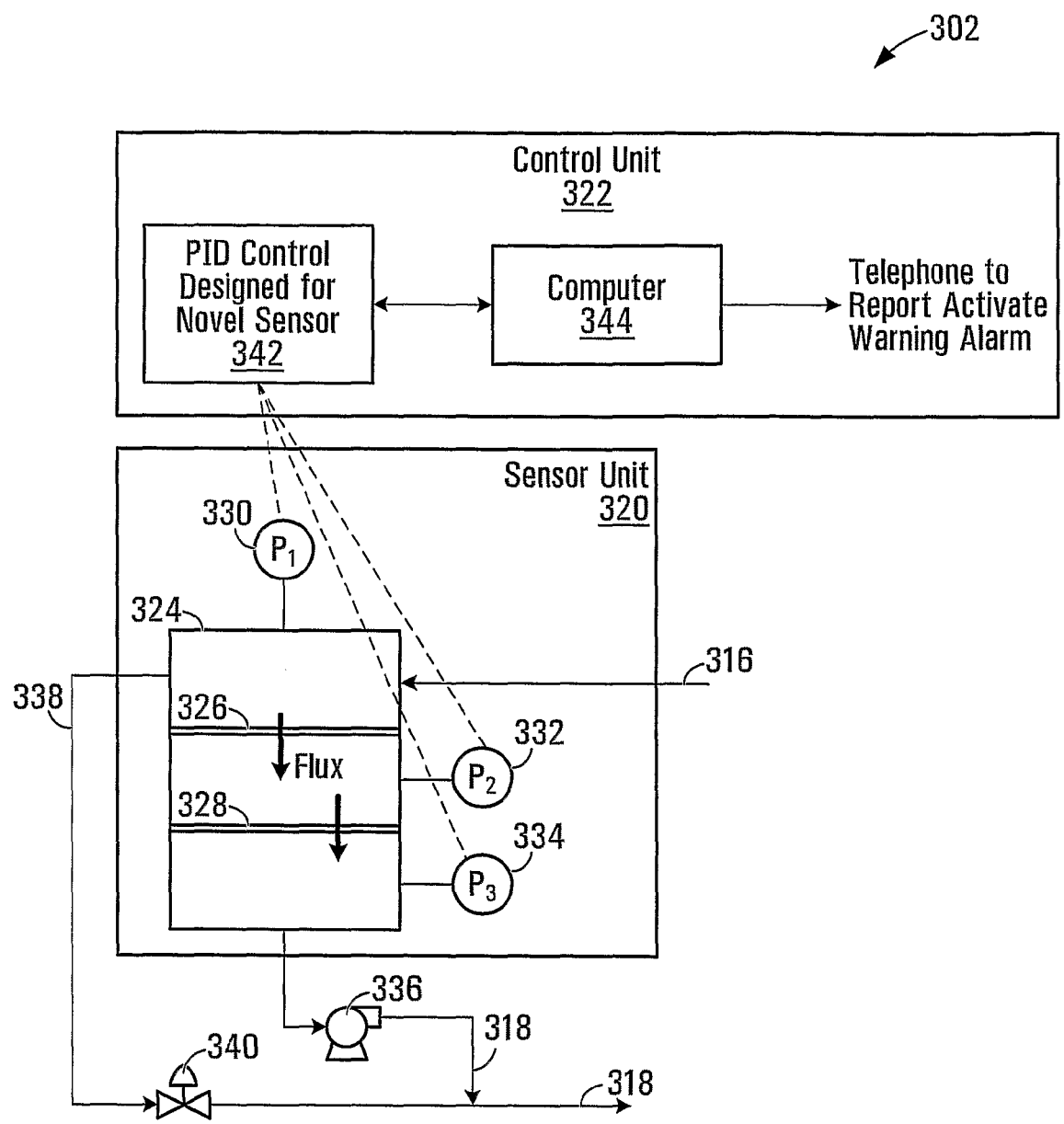
FIG. 4 is a schematic diagram of the membrane-based detector of FIG. 3.

Detector 302 is illustrated schematically in more detail in FIG. 4. Detector 302 includes a sensor unit 320 and a control unit 322.

Sensor unit 320 includes a membrane module 324 that is constructed similarly to module 101 shown in FIGS. 1A and 1B, and includes a first membrane 326 and a second membrane 328, and digital pressure transducers 330, 332, 334 as pressure sensors, disposed as shown. A micro pump 336 is installed in permeate line 318 for suction mode operation. A bypass pipeline 338 connects the feed side of first membrane 326 and permeate line 318 through a pressure adjustment valve 340. Valve 340 may be used to regulate the flow through pipeline 338 to selectively allow a portion of the effluent to bypass membrane module 324, in order to adjust the transmembrane pressures.

Each of pressure sensors 330, 332, 334 is in communication with a PID control module 342. Control module 342 is connected to a computer 344. Computer 344 may include hardware and software for operating control module 342 and other control components (not shown) within control unit 322. Computer 344 may also be in communication with an external electronic device, such as the control system for plant 300, or an output device (not shown) for presenting a signal, report, alarm, or the like to a user, as discussed above and can be understood by a person skilled in the art. The electronic communications within detector 302, and between detector 302 and an external electronic device may be by wired or wireless communication. Some of the communications may be wired and others may be wireless.

Computer 344 may utilize PID module 342 to provide improved stability, sensitivity, and lower signal noises. For instance, PID module 342 may take the pressures signals from the pressure sensors as input and output a proportional signal indicative of ratio $\pi$, and a derivative signal indicative of $d\pi/dt$. The output signals may then be processed by computer 344, such as described below. An integral signal indicative of an integral of $\pi$ over time may also be generated and used to perform additional calculations, as can be understood by those skilled in the art.

Computer 344 may be adapted, such as using software, or combination of software and hardware, to perform an exemplary logic or algorithm illustrated by the flow chart S500 shown in FIG. 5.

At S502, current values of pressures $P_1$, $P_2$, and $P_3$ are obtained based on the pressure signals received respectively from pressure sensors 330, 332, 334. The initial values of the pressures may be set by the user or set to zero. In some cases, $P_1$ or $P_3$ may be set to a constant, such as zero as shown. In such a case, it may not be necessary to detect or monitor the constant pressure.

At S504, π is calculated from $P_1$, $P_2$, and $P_3$ according to equation (1).

At S506, dπ/dt is calculated based on the current and previous values of π. The initial values of t, π, and dπ/dt may be set to zero.

The calculations at S504 and S506 may be carried out at computer 344 using the measured pressures. Alternatively, computer 344 may receive output signals indicative of π and dπ/dt from PID module 342.

At S508, π and dπ/dt are tested according to equation (2) to determine if any of them is within the respective pre-selected range. The values of the range parameters may be initialized earlier or input at S508, and may be adjusted during the monitoring process. A positive test result may require that at least one is, or both of π and dπ/dt are, within the pre-selected range, depending on the application. This is also true for S512 and S516 below.

When the test result is positive, a report may be communicated to a user indicating that the upstream membrane is working normally, at S510. The report may be communicated to the user in any suitable manner, such as to a computer output or over a network (not shown).

When the test result is negative, the next test is taken at S512 according to equation (4), to determine if one or both of π and dπ/dt are within the respective ranges.

If the test result is positive, a report may be communicated to a user, at S514, indicating that the status is abnormal and, for example, a foulant such as large particles, are present in the fluid.

If the test result is negative, the next test is taken at S516 according to equation (3), to determine if one or both of π and dπ/dt are higher than the respective threshold.

If the test result is positive, an alarm report may be communicated to the user at S518, indicating that the upstream membrane has failed, and there is a high concentration of foulant in the effluent from the upstream membrane.

Additional criteria may be tested and reported such as at S520, S522, S524, and S526.

Here, some other possible operating conditions may be identified. For example, it may be determined if there is any effluent flow received by the membrane sensor. Such a condition may be determined based on whether $dP_1/dt$, $dP_2/dt$, and $dP_3/dt$ are negative, and whether $P_1=P_2$ (or $P_1/P_2=1$). It may also be determined if any of membranes 102, 104 is broken. Failure of membrane 102 or 104 may be determined based on whether $dP_1/dt$, $dP_2/dt$, and $dP_3/dt$ are negative, and π is zero or near zero (indicating failure of membrane 102), or there is a sharp increase in π and dπ/dt (indicating failure of membrane 104).

At S528, the monitoring loop may terminate, or go to the next iteration by returning to S502. In the next iteration, the iteration index "n" is incremented by one, and the updated pressures values are used.

As can be appreciated, pressures $P_1$, $P_2$, and $P_3$ may be monitored continuously, on at regular intervals. Instead of the current, instantaneous pressure value, the average value of each pressure over a previous time interval may be used as the current pressure. Average values may be less susceptible to noises or other random fluctuations in the system.

Flow chart S500 is for illustration purposes only and may be modified or optimized by those skilled in the art.

The operation of detector 302 is similar to the detection apparatus 100 discussed above with appropriate modifications which will be apparent to those skilled in the art.

EXAMPLES

Setup

Figure 6:
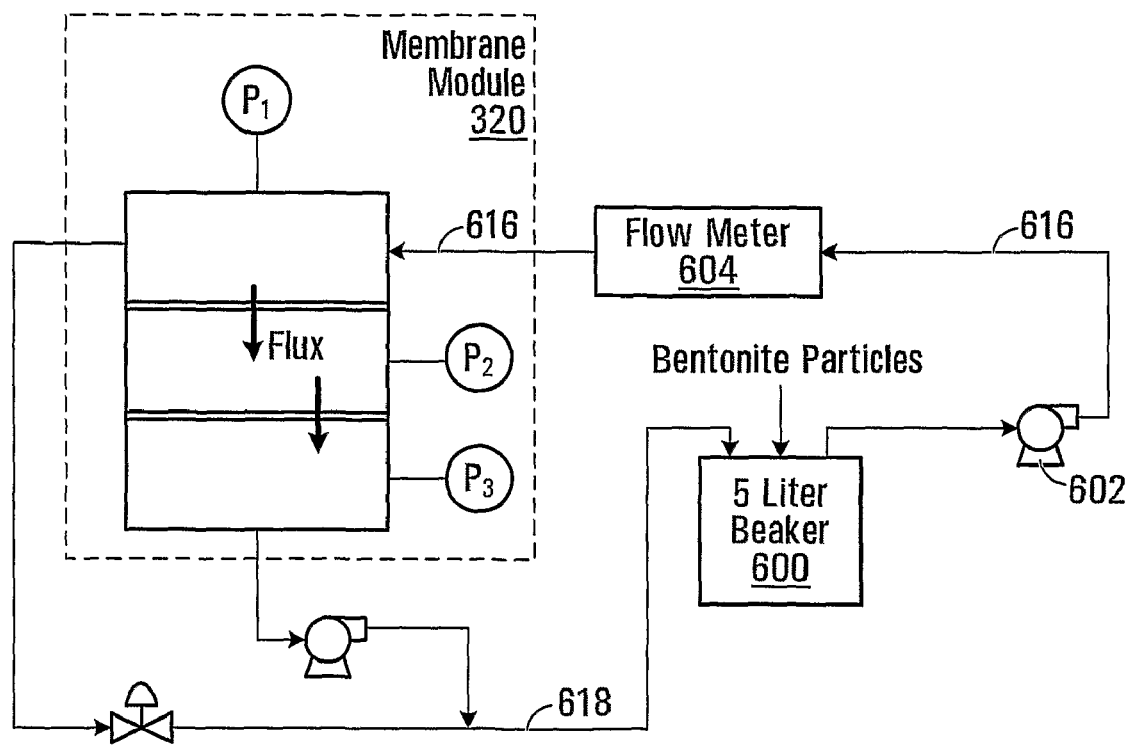
FIG. 6 is a schematic diagram of a testing system, for testing sample membrane-based detectors.

A membrane-based detector similar to detector 302 was constructed and tested. The sensor unit used in the tested detector is illustrated in FIG. 6. A control unit similar to control unit 322 was also included in the tested detector but is omitted in FIG. 6 for simplicity reasons. As can be seen in FIG. 6, the arrangement of the tested sensor unit was similar to sensor unit 320 shown in FIG. 4, except that the test detector was not connected to an actual membrane plant. Rather, the membrane module in the test detector was connected to a test beaker 600 through tubes 616 and 618, which formed a closed fluid loop. Beaker 600 had a volume of 5 liter. A fluid pump 602 was provided to drive the circulation of fluid within the loop. A flow meter 604 is disposed in input tube 616 for measuring the flow rate in tube 616.

Different membranes were tested. The membranes tested were formed of flat sheet membrane layers made of PVDF or CA. The total membrane area in the membrane sensor was 0.635 cm². The membrane layers used, their manufacturers and properties as provided by manufacturer are summarized in Table I. Each of the first and second membranes (see FIG. 6) of the membrane modules tested was formed of one or two membrane layers, as listed in Table II.

TABLE I

Membrane Layers

| Layer Type | Material | Source | Nominal pore size (μm) | Thickness (μm) | Porosity (%) |
|---|---|---|---|---|---|
| I | Hydrophilic | Millipore | 0.22 | 125 | 70 |
| II | PVDF | | 0.45 | 125 | 75 |
| III | Cellulose | Advantec | 0.2 | 125 | 66 |
| IV | acetate | MFS | 0.45 | 125 | 68 |
| V | | | 0.8 | 125 | 72 |

TABLE II

Sample Membrane Module

| Module Number | First Membrane | | Second membrane | |
|---|---|---|---|---|
| | First layer | Second Layer | First layer | Second layer |
| I | Type I | — | Type I | — |
| II | Type II | | Type II | |
| III | Type III | — | Type III | — |
| IV | Type IV | | Type III | |
| V | Type V | — | Type V | — |
| VI | Type V | Type IV | Type V | Type III |
| VII | Type III | — | Type II | — |

Example 1

Pressurization Mode

In the tests of this example, the flow rate through the membrane module was varied to vary $P_1$ and $P_2$, $P_3$ was relatively constant at about 1 atm. π was calculated according to equation (1). For calculating the response time, the following range and threshold constants were used: a=0, b=1.5, and c=3.

The test conducted included stability tests, sensitivity tests, and failure tests.

In a stability test, no foulant was added to the circulation of fluid flow, and $\pi$ was monitored to determine how it changed over time. The flow rate was varied in some cases to determine if it had any effect on the stability of $\pi$.

In a sensitivity test, a foulant was introduced into the circulation fluid (added to test beaker 600). The change in $\pi$ was monitored and a response time was determined, as an indicator of sensitivity. The apparent response time was the length of time between addition of the foulant to beaker 600 and the first instance when $\pi$ was found higher than the given threshold c. The actual or effective response time was the length of time between the first arrival of foulant at the feed side of the first (top) membrane in the detector and the first instance when $\pi$ was found higher than the given threshold. As can be appreciated, the effective response time equal to the difference between the apparent response time and the time it took the fluid to travel from beaker 600 to the feed side of the first membrane (referred to as the retention time in tube).

Example 1.1

Tap Water Tests

In this example, the feed fluid used in the testing was tap water, in some cases with bentonite particles dispersed therein as the foulant. The average bentonite particle size was 5 microns, determined using a laser scattering technique, with a particle size analyzer sold under the trademark MASTERSIZER 2000 from MALVERN INSTRUMENTS™. A cross flow was passed above the feed side of the top membrane in the membrane sensor, with a flow rate from 20 to 50 ml/min, and the corresponding Reynolds numbers from 61 to 411.

FIGS. 7A and 7B, and 8 to 11 show the results of tests conducted using Membrane Module I.

Figure 7A:
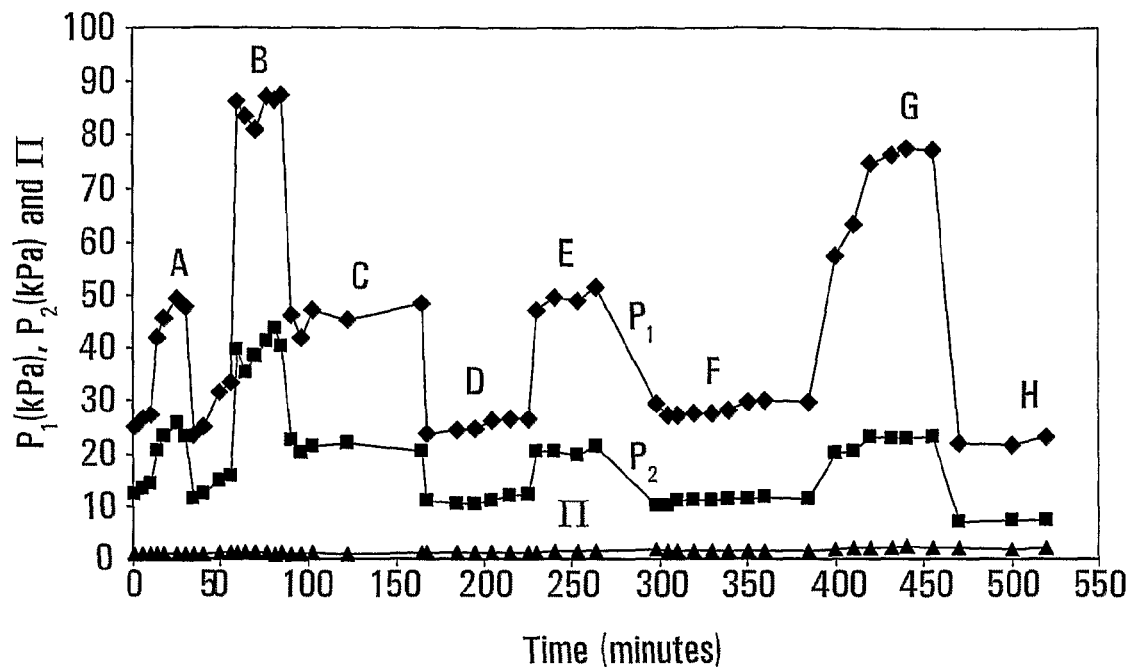
FIGS. 7A, 7B, 8 to 23, 24A and 24B are line graphs showing test results obtained from sample membrane-based detectors.
Figure 7B:
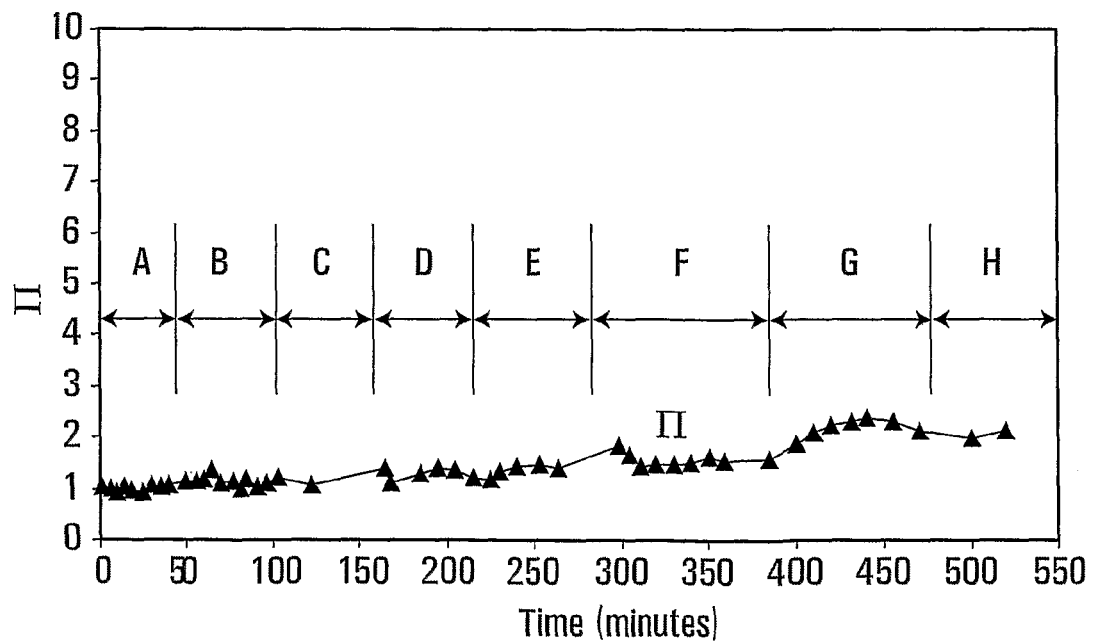

FIGS. 7A and 7B show results of stability tests conducted using tap water without bentonite particles. The flow rates in different time intervals were as follows (in ml/min): A-40; B-50; C-30; D-20; E-40; F-30; G-50; H-20. Generally, $P_2$ changed with $P_1$ in the same direction, and $\pi$ varied from 0.9 to 2.1. As can been seen in FIG. 7A, shortly after $P_1$ was increased to higher than 70 kPa, $P_2$ exhibited a dip or remained relatively constant, instead of increasing with $P_1$. This suggests that the process was not sustainable when the supply pressure $P_1$ was higher than 70 kPa, likely due to fouling caused by trace particles in the tap water. In this particular case, it was expected that to maintain good stability, the supply pressure $P_1$ should be lower than 70 kPa. It can be understood that the flow rate may also be limited to maintain stability. However, the maximum flow rate may change in different applications, as it may depend on other factors such as the contents of the feed fluid.

Figure 8:
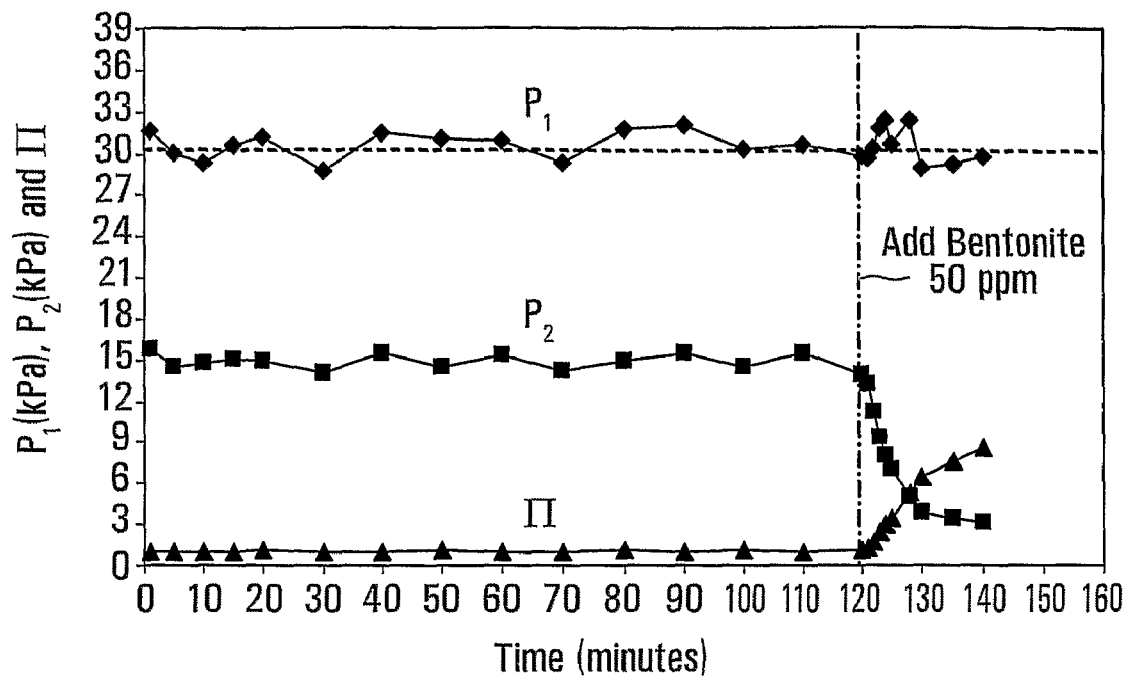

FIG. 8 shows the test results of sensitivity tests conducted using a mixture of tap water and bentonite. The operating pressure on the feed side of the top membrane was 30 kPa, and the flow rate was 30 ml/min. Initially, the fluid contained only tap water. A solution containing bentonite particles was injected into the tap water after two hours of operation. The bentonite concentration in the feed to the membrane was 50 mg/L (or 50 ppm). $\pi$ was monitored and was found to be relatively constant until bentonite addition. As can be seen from FIG. 8, bentonite particles were detected 8 minutes after their addition to the feed.

Figure 9:
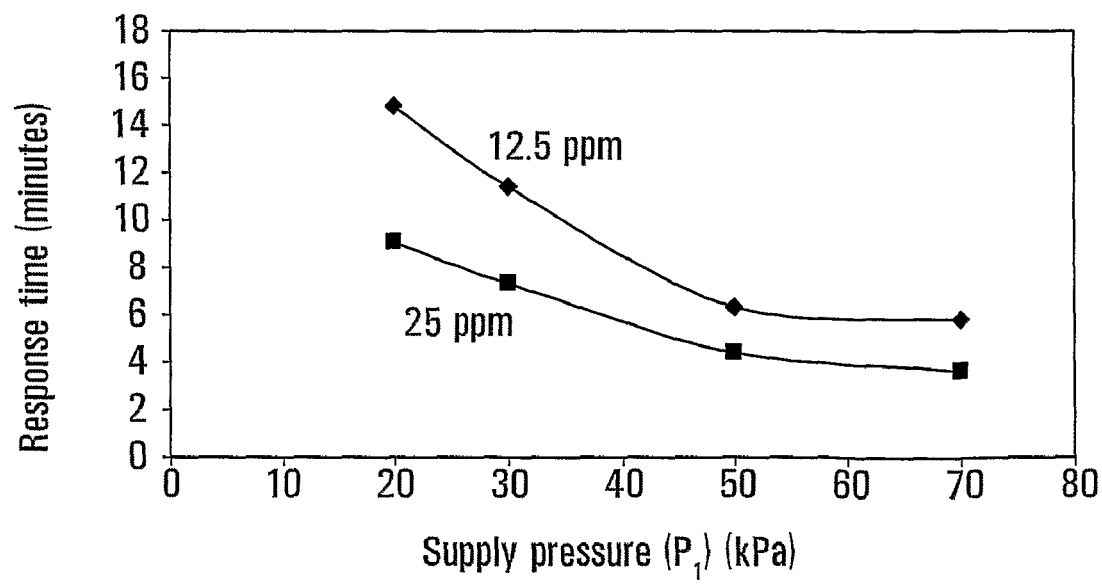

FIG. 9 shows the measured dependence of sensitivity on the supply pressure ($P_1$). The test conditions were the same as those for FIG. 8, except $P_1$ was varied. When $P_1$ increased, the response time decreased, indicating that the sensitivity increases with the supply pressure. Without being limited to any particular theory, this is likely because in the pressurization mode, the supply pressure is proportional to the flow rate, and a higher supply pressure can promote faster particle deposition on the membrane surface in the sensor module.

Figure 10:
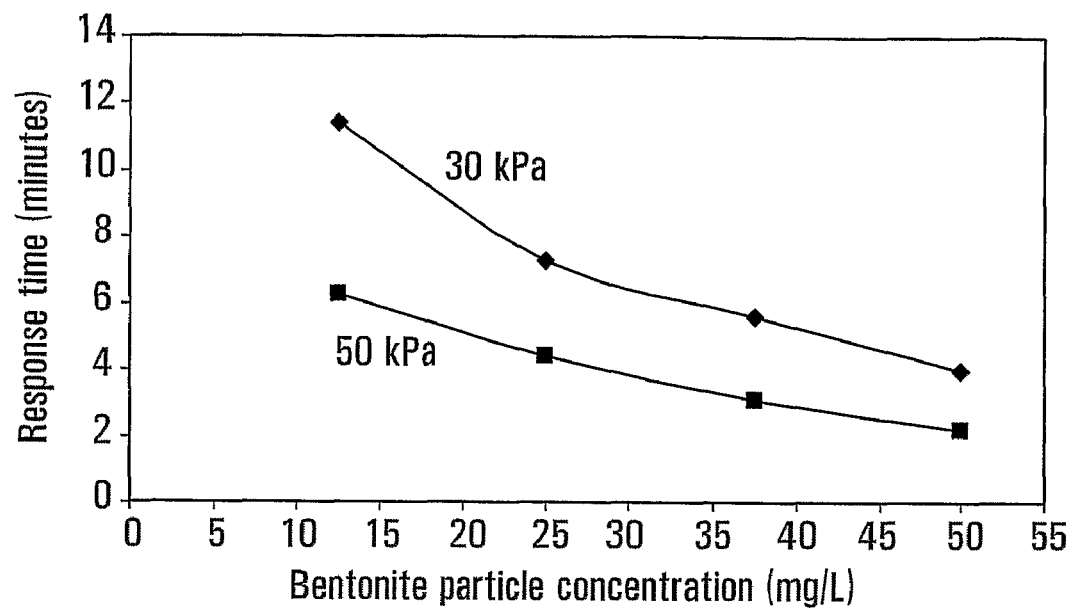

The bentonite concentration was also varied to study the sensitivity dependence on bentonite concentration. Results were obtained for two different bentonite concentrations, 50 and 12.5 mg/L, at two different supply pressures, 30 and 50 kPa. The results are shown in FIG. 10. It was found that, as expected, the sensitivity is higher at higher bentonite concentrations. For instance, at 50 kPa, the response time was 6 minutes for 12.5 mg/L of bentonite, and about 2 minutes for 50 mg/L of bentonite.

Figure 11:
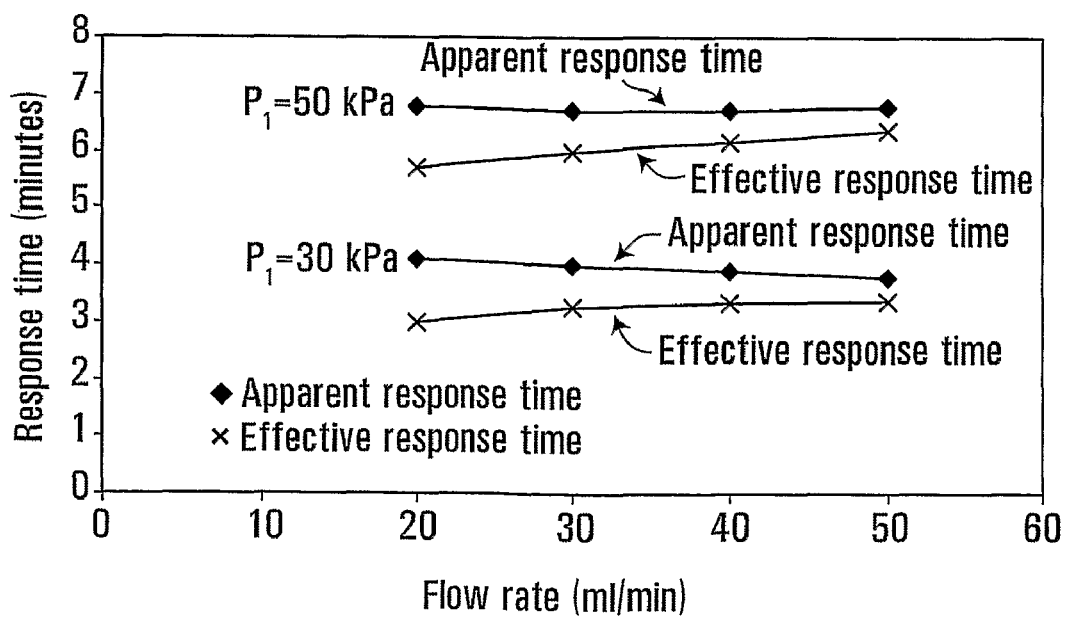

The effect of flow rate on the response time is shown in FIG. 11. Apparent response times were relatively constant with varying flow rates, but effective response times increased slightly when the flow rate was changed, resulting in a change in supply pressure from 30 to 50 kPa. The sensitivity decreased with increasing flow rate likely because higher shear stresses in the flow reduced particle deposition rate on the membrane surface.

Figure 12:
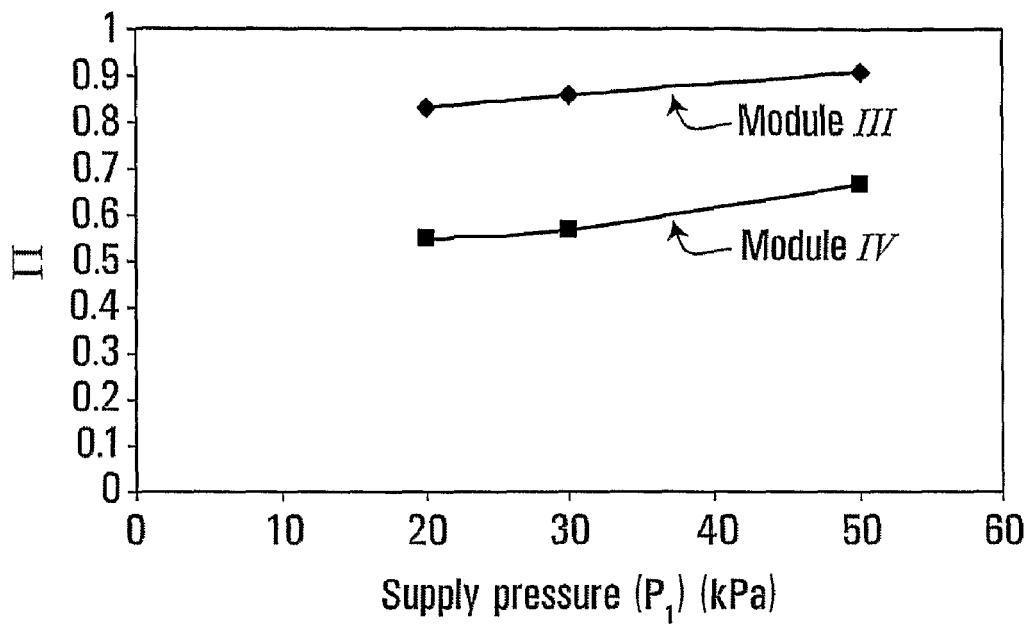
Figure 13:
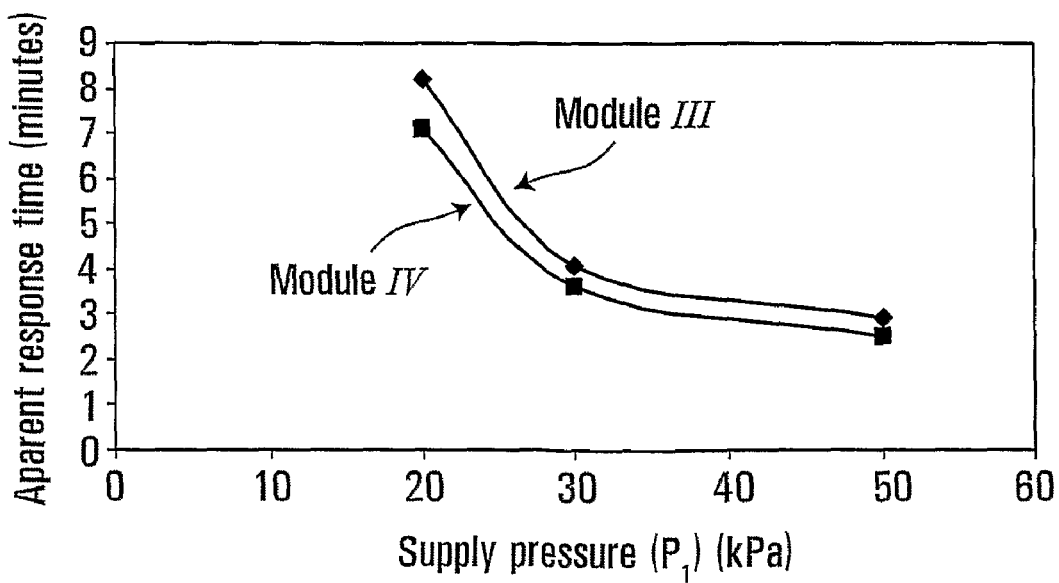

FIGS. 12 and 13 shows results obtained using Modules III or IV, with a flow rate of 30 ml/min. As shown in FIG. 12, $\pi$ was relatively stable in both cases over the supply pressure range of 20 to 50 kPa, with tape water. FIG. 13 shows the apparent response time after adding 25 mg/L bentonite. Shorter response time and better sensitivity (by 10-15%) was exhibited by Module IV, as compared to Module III.

Figure 14:
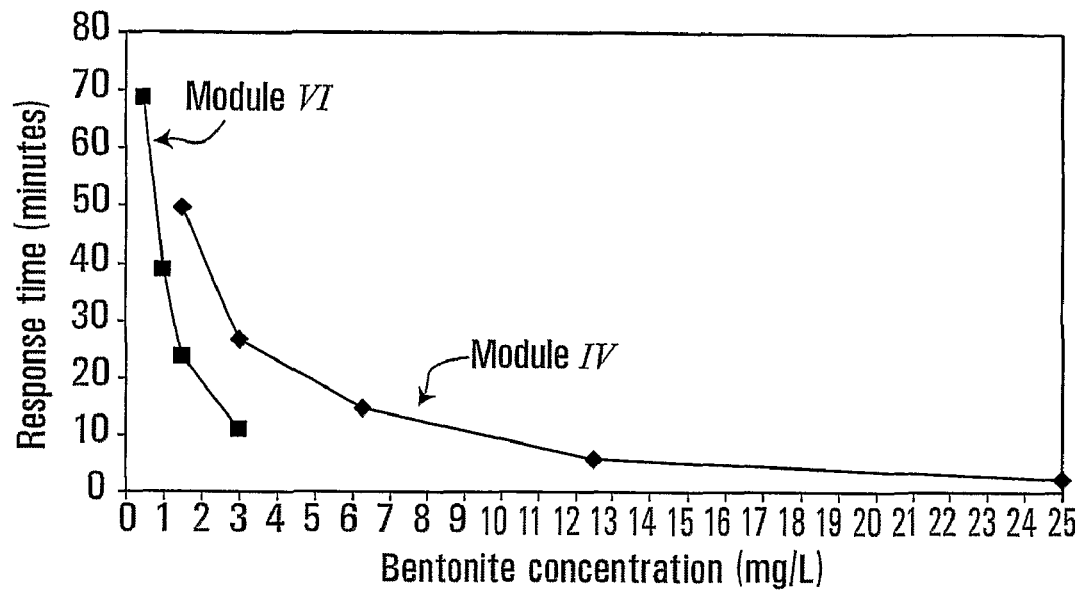
Figure 15:
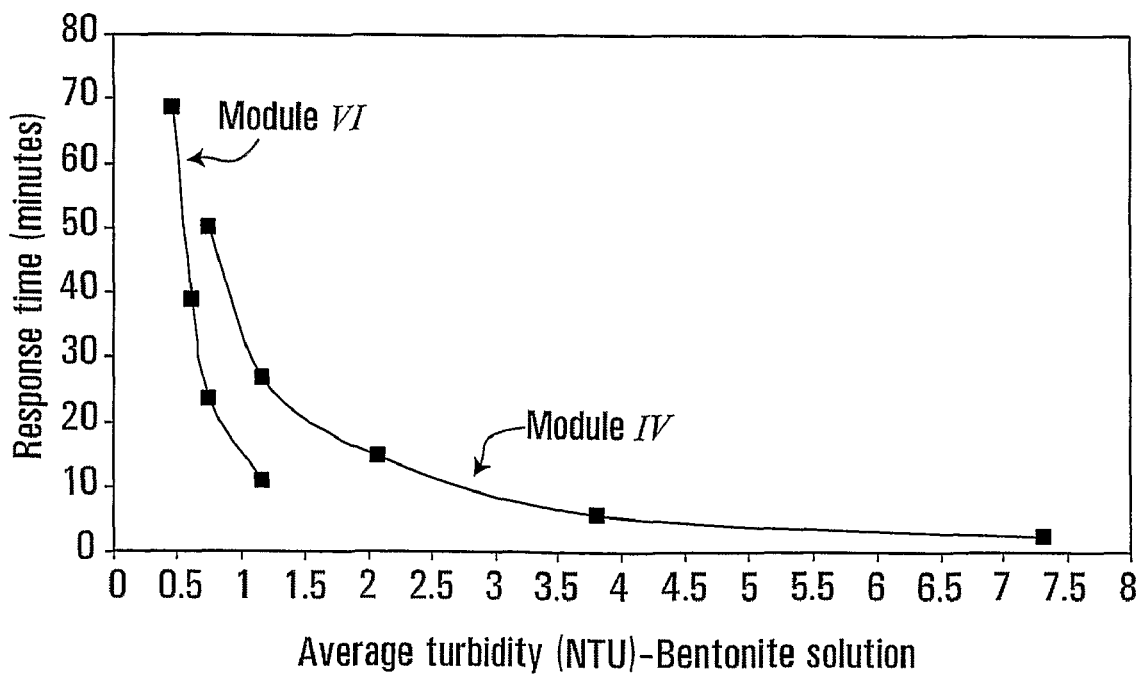

FIGS. 14 and 15 show the test results obtained using Modules IV and VI. FIG. 14 shows response times measured for both modules at various bentonite concentrations. The flow rate was 30 ml/min and the supply pressure was 50 kPa. Shorter response times were observed with Module VI (double-layered), by more than an half, as compared to Module IV (single-layered). For bentonite concentration of 0.5 mg/L, the response time was about 1 hour.

For comparison purposes, the bentonite concentrations were also measured using conventional standard turbidity meters, including both infrared and white light turbidity meters. The results showed that these meters were relatively insensitive to bentonite concentrations lower than 1 mg/L. In comparison, Module VI can detect bentonite concentrations at least as low as 0.5 mg/L. Even lower concentrations may be possible if longer response time is acceptable.

The measured response time dependence on turbidity is shown in FIG. 15. The response time for detecting bentonite at a turbidity from 0.5 to 1 NTU was from about 10 to 60 minutes.

Example 1.2

Wastewater Tests

In this example, the test setup was similar to in Example 1.1, but the test detector was connected to a submerged membrane bioreactor (MBR) unit. The test detector included a Membrane Module IV. The influent to the MBR was wastewater. The effluent from the MBR was fed to the test detector.

The influent (wastewater) fed to the MBR had a mixed liquor suspended solid (MLSS) concentration of 8 to 10 g/L, a pH of 6 to 7, and a chemical oxygen demand (COD) of 265 mg/L. The effluent (permeate) from the MBR had 5 mg/L of total organic carbon, a pH of 6 to 6.5, and a color of 35 to 39 mg Pt/L. 1 ppm of NaOCl was added to the effluent from the MBR (feed to the membrane sensor) to improve stability. The supply pressure at the feed side of the first membrane in the test detector was 50 kPa (gauge), and the flow rate was 30 ml/min.

Simulated-Failure Test

Figure 16:
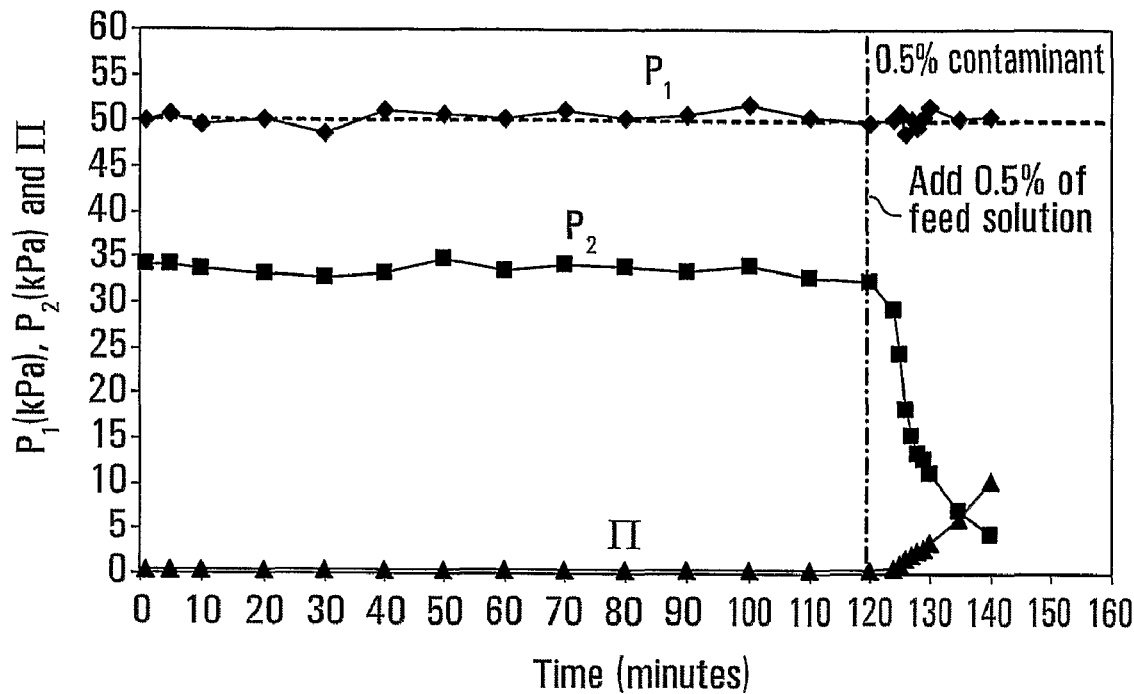

FIG. 16 shows measured values of $P_1$ and $P_2$, and calculated values of $\pi$, as functions of time. Initially, the membrane sensor was fed with the effluent from the MBR with no added contaminant. After 120 minutes, unfiltered wastewater was added to the effluent, to a concentration of 0.5%, to simulate leaking of the MBR filtration membrane. The contaminated effluent was then fed to the membrane sensor. As can be seen, the membrane sensor exhibited both good stability and sensitivity.

Figure 17:
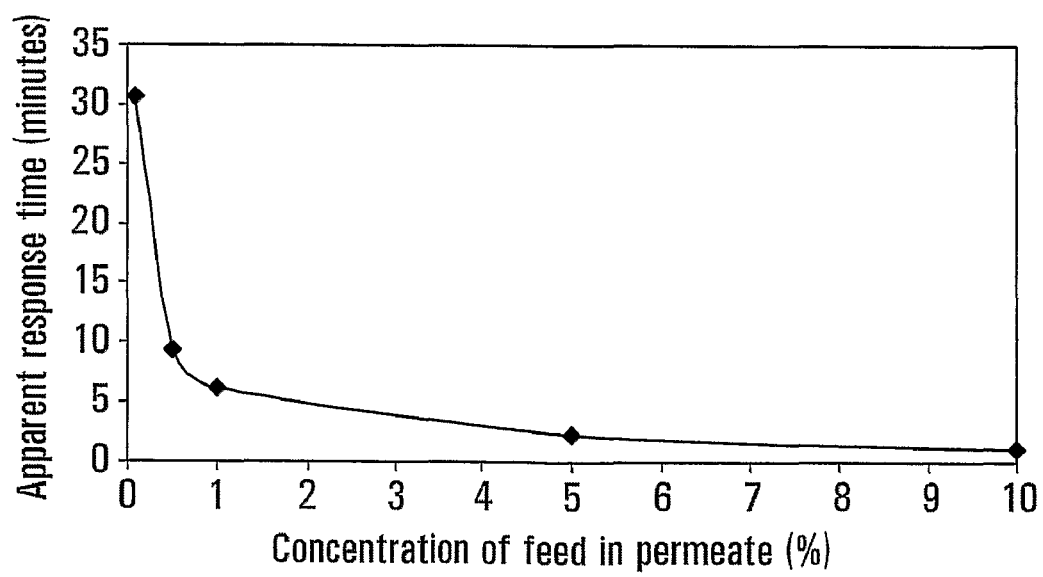

FIG. 17 shows the dependence of the apparent response time on contaminant concentration, which was varied by varying the concentration of added influent in the effluent. The lowest concentration was 0.1%, which corresponded to a response time of 31 minutes.

Example 1.3

Failure Test

In this example, a membrane detector with Membrane Module IV was used to detect the failure of flat-sheet microfiltration (MF) membrane modules. Each MF module included a Type III membrane layer obtained from SATURI-UST™ (Germany). The MF module had a 338 cm$^2$ membrane area. The membrane material had 0.2 micron pore size and a diameter of 29.3 cm. Membrane failure was simulated by creating a pinhole in the MF membrane, with a pinhole diameter of about 0.7 mm. One pinhole was made on one side of the membrane in the MF module.

A solution containing 500 mg/L of bentonite particles was used as the influent. The supply pressure was 50 kPa. The total effluent flow rate from the MF module was 100 ml/min, and the flow rate through the membrane sensor was 30 ml/min. Fluid flow was driven with a mechanical overhead stirrer operating at 500 rpm.

Figure 18:
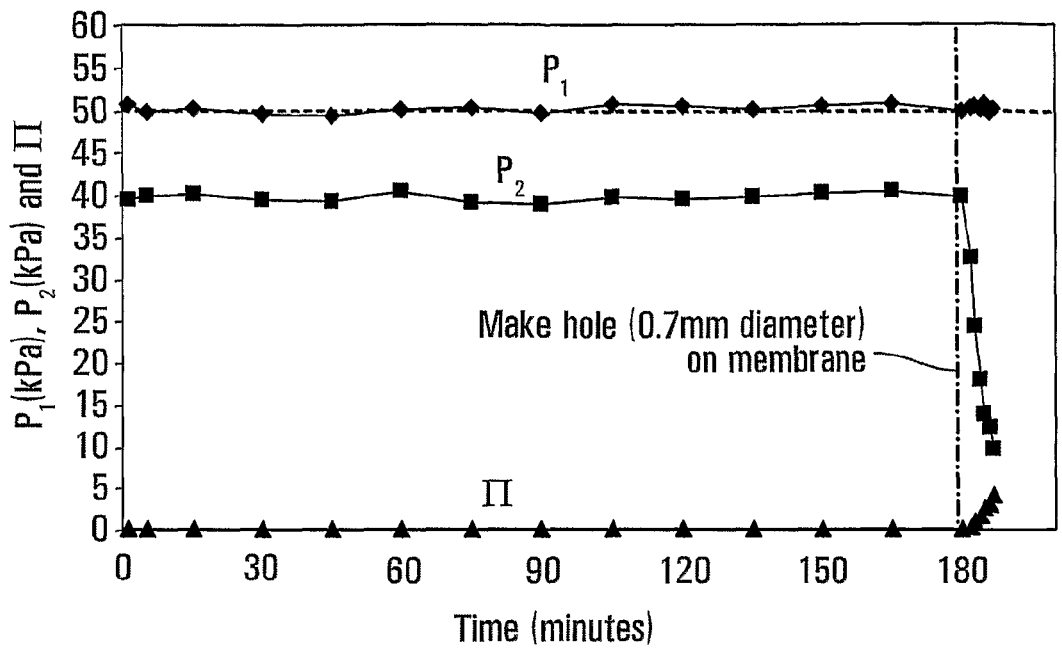

Test results are shown in FIG. 18. The ratio $\pi$ was calculated using equation (1). The pinhole was created at the 180th minute. The presence of bentonite particles was detected within two minutes, and membrane failure was detected within about 6 minutes.

Example 2

Suction Mode

The tests under this Example were conducted in the suction mode.

In this example, the test setup and conditions were similar to those in EXAMPLE 1, except that the membrane sensor was operated in the suction (vacuum) mode and that the membrane area in the membrane sensor was 0.63 cm$^2$ and the flow rates above the surface of the first membrane in the membrane sensor ranged from 30 to and 80 ml/min with the corresponding Reynolds numbers of 211 to 423.

For this Example, $\pi$ was calculated according equation (1).

Example 2.1

Particle Detection Test

Figure 19:
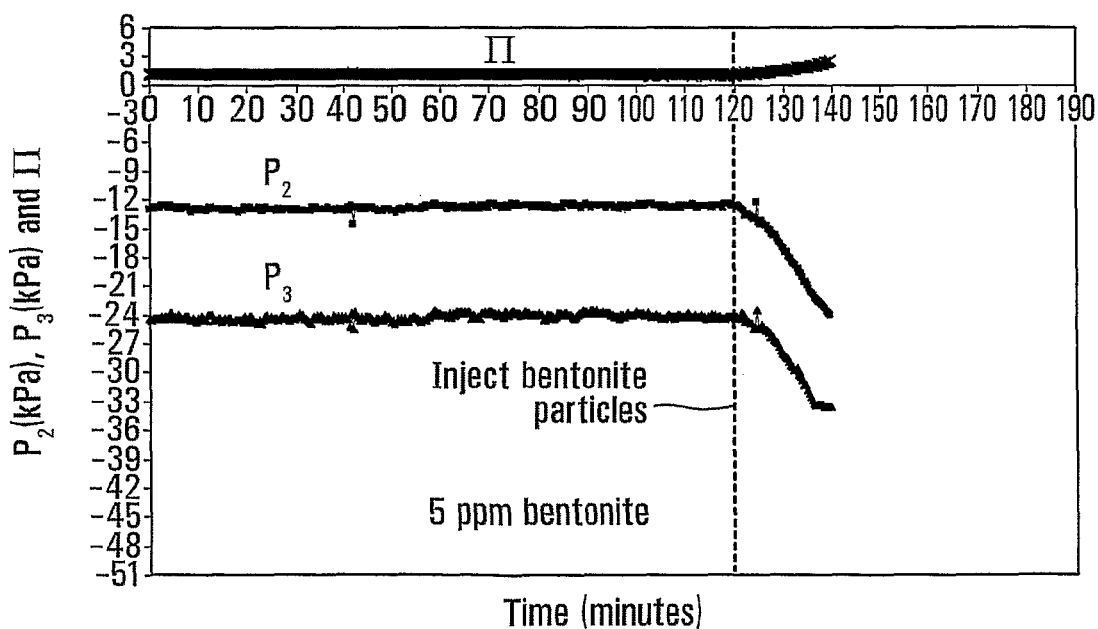
Figure 20:
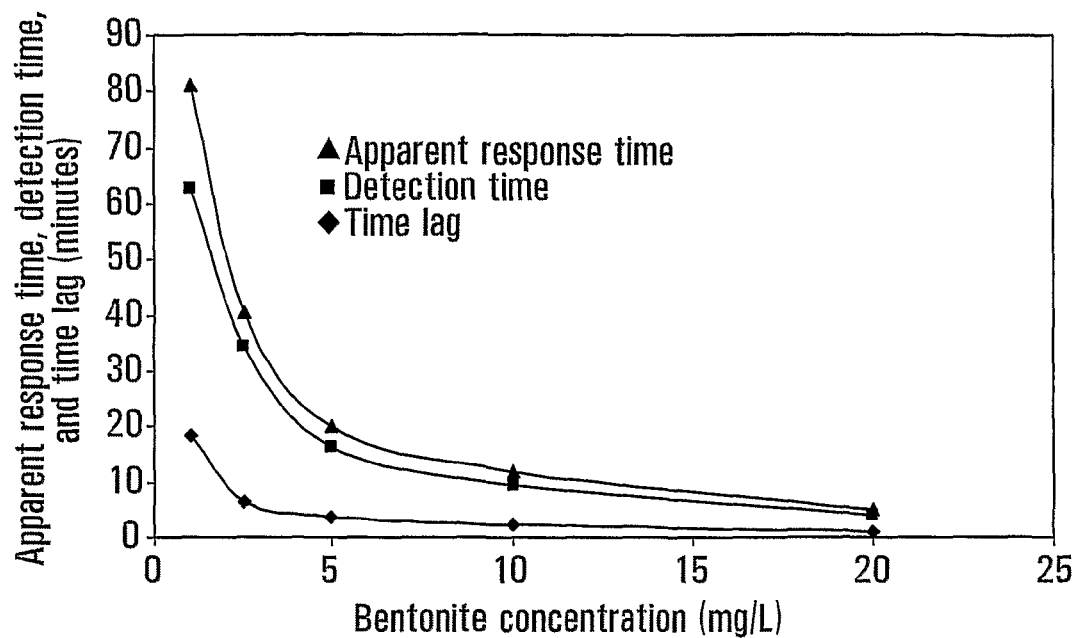

FIGS. 19 and 20 show the test results obtained using membrane Module I in the membrane detector. The testing conditions were: a=0, b=1.23, c=2.46, and the flow rate was 30 ml/min and the pressure $P_1$ was zero (gauge). For FIG. 19, the concentration of injected bentonite particles was 5 ppm. Before bentonite injection, $\pi$ was stable over 2 hours at 1.13 and $P_2$ and $P_3$ were relatively constant at −12.8 and −24.5 kPa, respectively. The retention time in the tubing 616 was about 30 s. After bentonite injection, $P_2$ and $P_3$ both decreased and, consequently, $\pi$ increased, continuously. FIG. 20 shows the apparent response time, the detection time, and the time lag at different bentonite concentrations. For the bentonite concentration of 1 ppm, the detection time and the time lag were 62.7 and 18.3 minutes, respectively.

Figure 21:
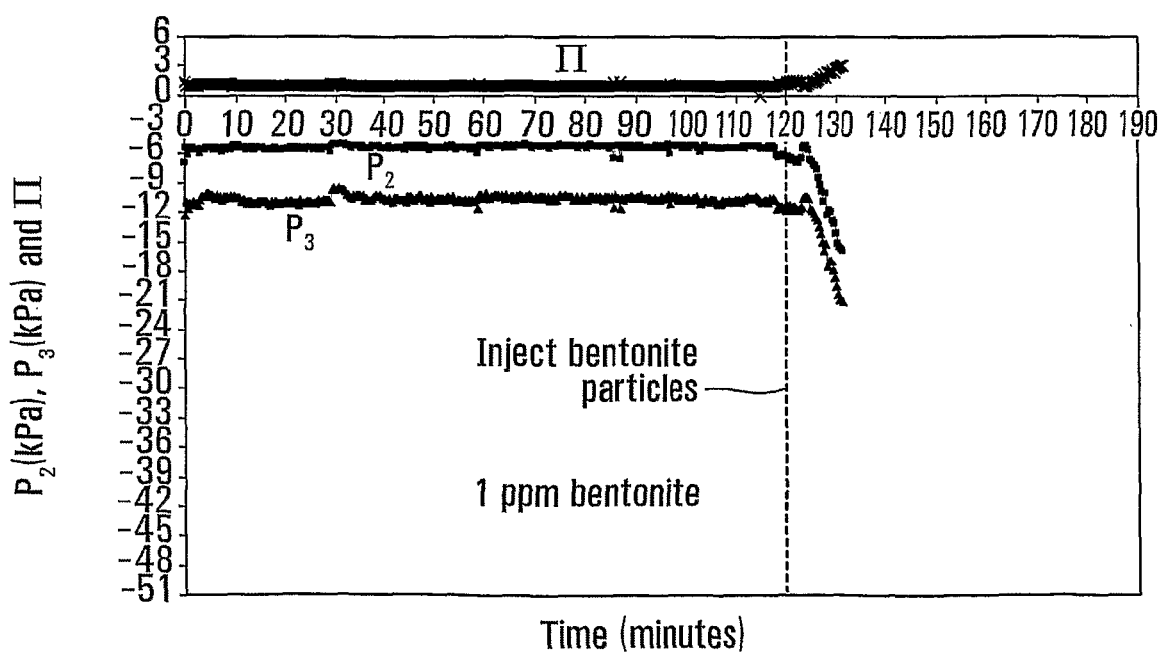
Figure 22:
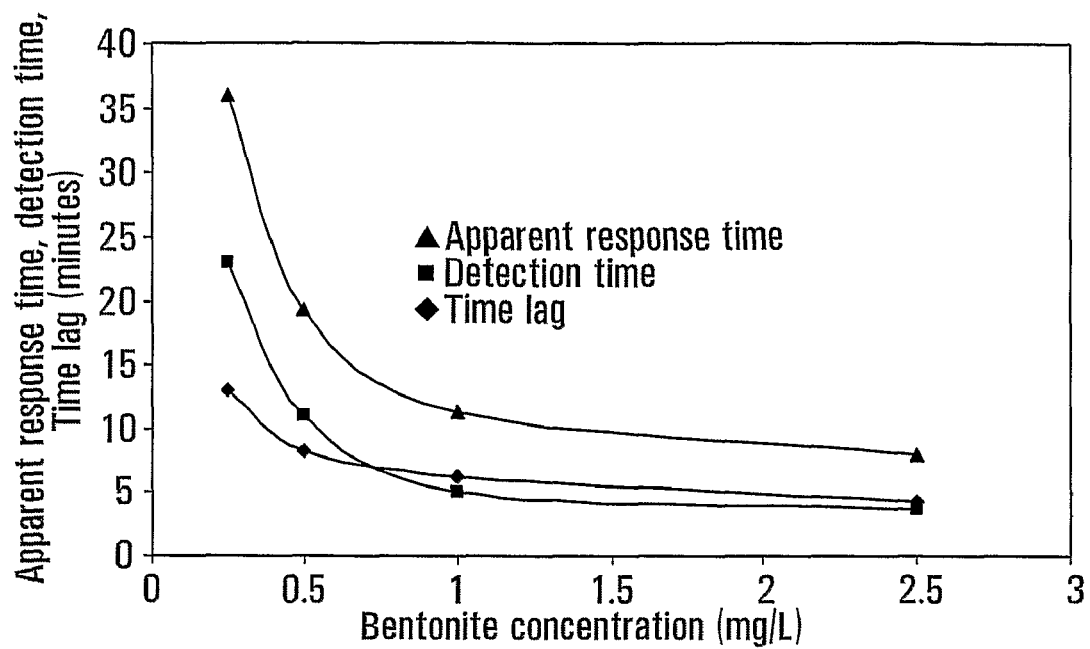

FIGS. 21 and 22 show results of tests conducted with Module II. For FIG. 21, the conditions were similar to those for FIG. 19, except that the bentonite concentration was only 1 ppm. Before bentonite injection, $\pi$ was stable over 2 hours at 1.11 and $P_2$ and $P_3$ were relatively constant at −5.3 and −10.1 kPa, respectively. The apparent response time in this case was 11.3 min. As shown in FIG. 22, the time lag was comparable to the detection time when the bentonite concentration was higher than 1 ppm, and shorter than detection time the bentonite concentration was lower than 1 ppm. It appears that Module II provided higher sensitivity than Module I.

Figure 23:
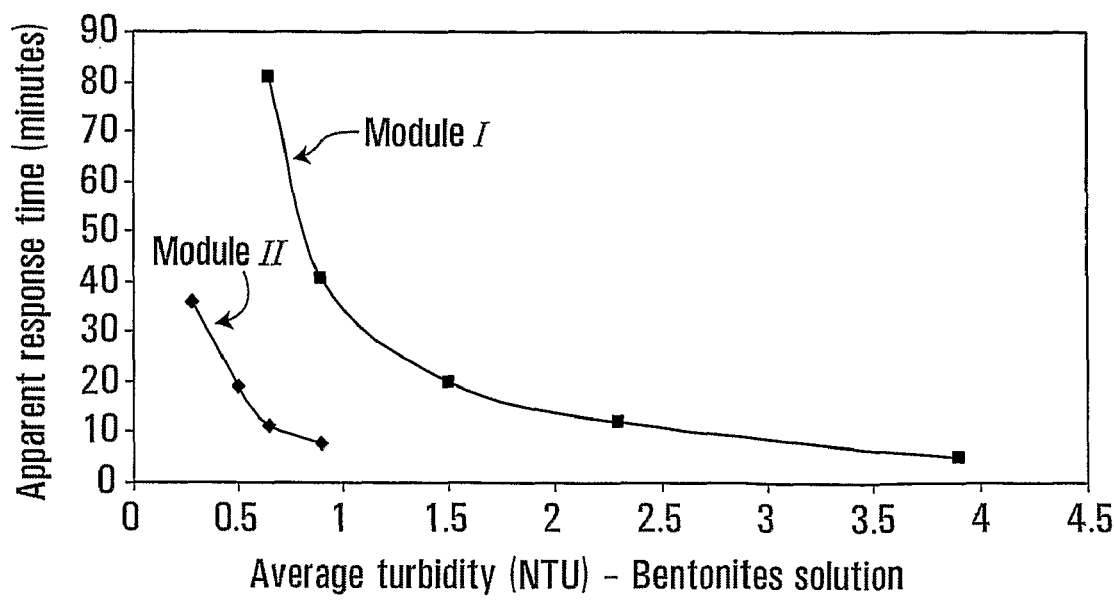

FIG. 23 compares the dependence of apparent response time on turbidity between Modules I and II. As shown, Module II detected the particles at 0.3 NTU in 36 minutes.

Example 2.2

Failure Test

The filtration membrane module included four double-face flat-sheet MF membrane modules, which use Type III membranes. Bubbling and an overhead stirrer at 300 rpm were used to control fouling and cake deposition for the bentonite solution microfiltration. The gaps between the flat sheet modules were 6 mm, and coarse bubbles were used. The permeate flow rate was 80 ml/min and flowed directly to the membrane-based detector for integrity detection. The concentration of the bentonite solution was 1.5 g/L with fixed concentration mode and permeate recycle.

Figure 24A:
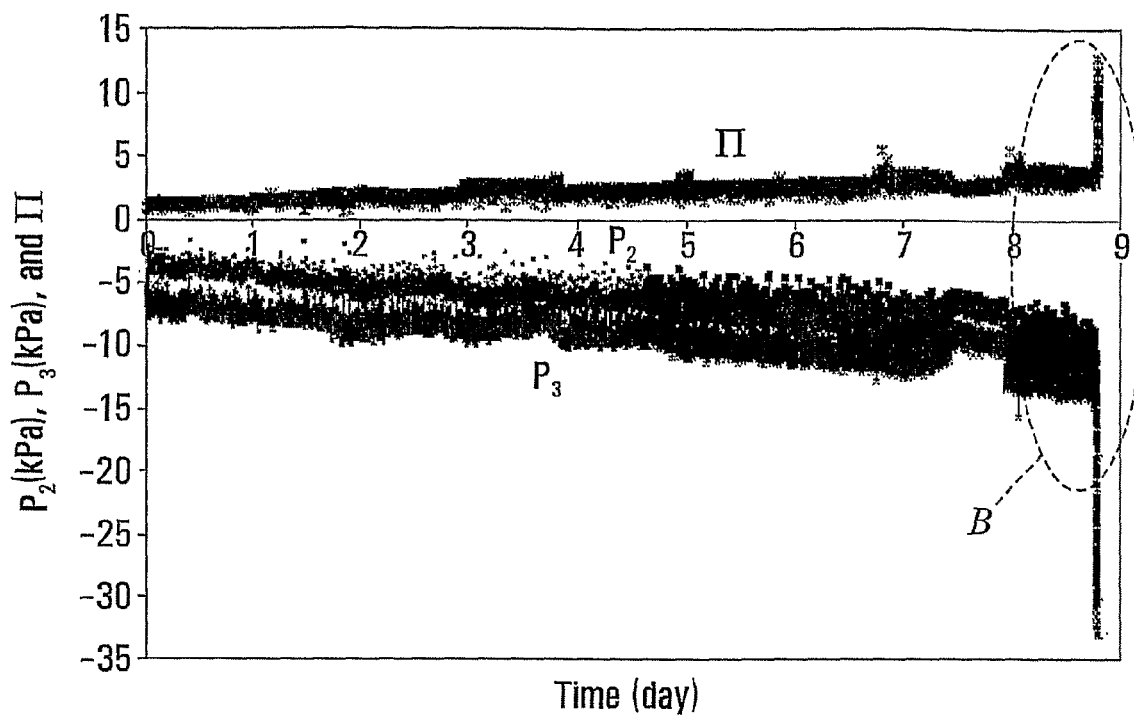
Figure 24B:
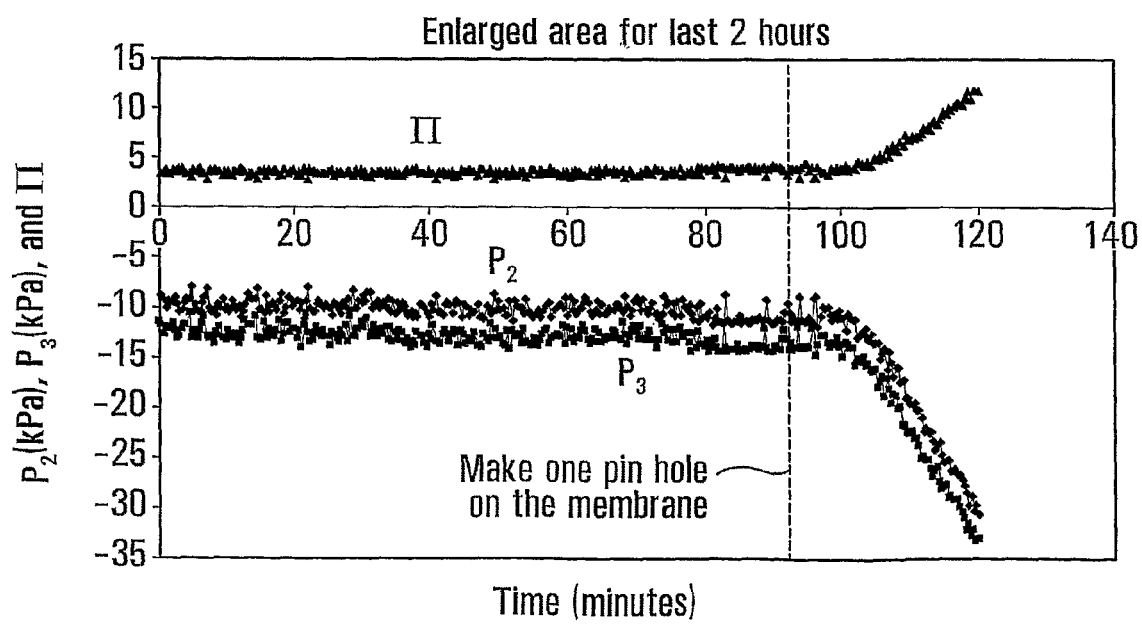

FIGS. 24A and 24B show the measured $P_2$ and $P_3$ and calculated $\pi$ over a one-week period. FIG. 24B shows the portion of graph enclosed in the dashed line in FIG. 24A. Based on experimental data, it appeared that small particles were present in the permeate stream from the MF membrane. The slow initial decrease of $P_2$ and $P_3$ shown in FIG. 24A was likely due to slow fouling resulting from small particles that passed through the MF membrane.

After 5 days, $P_2$, $P_3$, and $\pi_1$ became relatively stable at −10 kPa, −13.3 kPa, and 3.8 respectively. The range and threshold constants were selected as a=0, b=4.5, and c=9.

After 8 days, a pinhole was made on one side of the membrane in the MF module. The pinhole diameter was approximately 0.8 mm. The presence of bentonite particles in the effluent was detected within 17 min (apparent response time) of making the pinhole. The turbidity of the contaminated permeate after the membrane process failure was 1.9 NTU.

As can be discerned from FIGS. 24A and 24B, as well as FIGS. 8, 16, 18, 19, and 21, the value of $d\pi/dt$, which is the slope of the line that connects the $\pi$ points, also increased substantially subsequent to the introduction of the foulant into the feed to the membrane detector. For example, in the case shown in FIGS. 24A and 24B, the calculated values of $d\pi/dt$ were 0.001 before the pinhole was created, but increased by about 10 times to 0.01 after the pinhole was made.

Other features, benefits and advantages of the embodiments described herein not expressly mentioned above can be understood from this description and the drawings by those skilled in the art.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A method for detecting failure of a filtration membrane, comprising:
   directing an effluent from said filtration membrane to permeate through a first permeable membrane, and from said first permeable membrane to permeate through a second permeable membrane;
   determining a ratio between $(P_1-P_2)$ and $(P_2-P_3)$, $P_1$ being a first pressure at a feed side of said first permeable membrane, $P_2$ being a second pressure between said first and second permeable membranes, and $P_3$ being a third pressure at a permeate side of said second permeable membrane; and
   correlating said ratio with a failure of said filtration membrane.

2. The method of claim 1, wherein said correlating comprises determining that said filtration membrane is in a failed state when at least one of said ratio and a time derivative of said ratio is higher than a respective pre-defined threshold.

3. The method of claim 2, wherein said respective pre-defined threshold for said ratio is 3, and said respective threshold for said derivative of said ratio is 0.01.

4. The method of claim 1, further comprising correlating said ratio with the presence of a foulant in said effluent.

5. The method of claim 4, wherein said correlating said ratio with the presence of said foulant in said effluent comprises determining that said foulant is present in said effluent when said ratio is within a pre-defined range.

6. The method of claim 5, wherein said pre-defined range is from 1.5 to 3.

7. The method of claim 1, wherein said determining a ratio comprises sensing said first, second, and third pressures, and calculating said ratio at time t, $\pi(t)$, as $\pi(t)=[P_1(t)-P_2(t)]/[P_2(t)-P_3(t)]$.

8. The method of claim 1, comprising presenting a correlation result to a user.

9. The method of claim 1, wherein the flow rate through said first and second permeable membranes is from 1 to 500 ml/min.

10. The method of claim 1, wherein the gauge pressure in the feed to said first membrane is from 1 to 95 kPa, and the gauge pressure in the permeate side of said second membrane is from −100 to 100 kPa.

11. The method of claim 1, comprising establishing a pressure difference across said first and second permeable membranes, said pressure difference being between 0 and 1,000 kPa.

12. An apparatus for detecting failure of a filtration membrane, comprising:
   a first permeable membrane and a second permeable membrane, each having a feed side and a permeate side;
   a conduit for directing an effluent from said filtration membrane to said first permeable membrane and from said first permeable membrane to said second permeable membrane;
   a first pressure sensor for producing a pressure signal indicative of a first pressure, $P_1$, at said feed side of said first permeable membrane;
   a second pressure sensor for producing a pressure signal indicative of a second pressure, $P_2$, between said first and second permeable membranes;
   a third pressure sensor for producing a pressure signal indicative of a third pressure, $P_3$, at said permeate side of said second permeable membrane; and
   a data processing unit in communication with each one of said plurality of pressure sensors, for
      receiving pressure signals from said pressure sensors,
      calculating a ratio between $(P_1-P_2)$ and $(P_2-P_3)$ based on said pressure signals; and
      correlating said ratio with a failure of said filtration membrane.

13. The apparatus of claim 12, wherein said ratio at time t is $\pi(t)$, calculated as $\pi(t)=[P_1(t)-P_2(t)]/[P_2(t)-P_3(t)]$.

14. The apparatus of claim 12, wherein said correlating comprises determining that said filtration membrane is in a failed state when at least one of said ratio and a time derivative of said ratio is higher than a respective pre-defined threshold.

15. The apparatus of claim 14, wherein said respective threshold for said ratio is 3, and said respective pre-defined threshold for said time derivative of said ratio is 0.01.

16. The apparatus of claim 12, wherein said data processing unit is adapted to correlate said ratio with the presence of a foulant in said effluent.

17. The apparatus of claim 16, wherein said data processing unit is adapted to determine that said foulant is present in said effluent when said ratio is within a pre-defined range.

18. The apparatus of claim 17, wherein said pre-defined range is from 1.5 to 3.

19. The apparatus of claim 12, further comprising a fluid pump for establishing a pressure difference across said first and second permeable membranes to drive fluid flow through said first and second permeable membranes.

20. The apparatus of claim 19, wherein said pressure difference is between 0 and 1,000 kPa.

21. The apparatus of claim 12, wherein at least said first permeable membrane has an average pore size from 0.05 to 5 microns.

22. The apparatus of claim 12, wherein at least said first permeable membrane comprises a plurality of membrane layers.

23. A fluid treatment system comprising the apparatus of claim 12 and a filtration membrane, said apparatus in fluid communication with said filtration membrane for receiving an effluent therefrom.

24. The fluid treatment system of claim 23, further comprising a control unit for controlling operation of said fluid treatment system, said control unit in communication with said data processing unit for controlling said operation in response to said correlating.

25. A method of detecting a foulant in a fluid, comprising:
   directing said fluid to permeate through a first permeable membrane and from said first membrane to permeate through a second permeable membrane;
   determining a ratio between $(P_1-P_2)$ and $(P_2-P_3)$, $P_1$ being a first pressure at a feed side of said first permeable membrane, $P_2$ being a second pressure between said first and second permeable membranes, $P_3$ being a third pressure at a permeate side of said second permeable membrane; and
   correlating said ratio with the presence of said foulant in said fluid.

26. The method of claim 25, wherein said correlating comprises determining that said foulant is present in said fluid when said ratio is higher than a pre-defined threshold.

27. The method of claim 26, wherein said pre-defined threshold is 1.5.

28. The method of claim 25, said determining a ratio comprises sensing said first, second, and third pressures, and calculating said ratio at time t, $\pi(t)$, as $\pi(t)=[P_1(t)-P_2(t)]/[P_2(t)-P_3(t)]$.

29. An apparatus for detecting a foulant in a fluid, comprising:
- a first permeable membrane and a second permeable membrane, each having a feed side and a permeate side;
- a conduit for directing said fluid to said first permeable membrane and from said first permeable membrane to said second permeable membrane;
- a first pressure sensor for generating a first pressure signal indicative of a first pressure, $P_1$, at said feed side of said first permeable membrane;
- a second pressure sensor for generating a second pressure signal indicative of a second pressure, $P_2$, between said first and second permeable membranes;
- a third pressure sensor for generating a third pressure signal indicative of a third pressure, $P_3$, at said permeate side of said second sensor; and
- a data processing unit in communication with each one of said pressure sensors, for
  - receiving said pressure signals from said pressure sensors,
  - calculating a ratio between $(P_1-P_2)$ and $(P_2-P_3)$ based on said pressure signals; and
  - correlating said ratio with the presence of said foulant in said fluid.

30. The apparatus of claim 29, wherein said ratio at time t is $\pi(t)$, calculated as $\pi(t)=[P_1(t)-P_2(t)]/[P_2(t)-P_3(t)]$.

31. The apparatus of claim 29, wherein said correlating comprises determining that said foulant is present in said fluid when said ratio is higher than a pre-defined threshold.

32. The apparatus of claim 31, wherein said pre-defined threshold is 1.5.

33. The apparatus of claim 29, wherein at least said first permeable membrane has an average pore size from 0.05 to 5 microns.

* * * * *